(12) United States Patent (10) Patent No.: US 10,606,374 B2
Park et al. (45) Date of Patent: Mar. 31, 2020

(54) WATCH-TYPE MOBILE TERMINAL

(71) Applicant: LG ELECTRONICS INC., Seoul (KR)

(72) Inventors: Jisoo Park, Seoul (KR); Hongjo Shim, Seoul (KR); Hyunwoo Kim, Seoul (KR); Hyunok Lee, Seoul (KR); Youngho Sohn, Seoul (KR); Mihyun Park, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 30 days.

(21) Appl. No.: 15/753,144

(22) PCT Filed: Sep. 1, 2015

(86) PCT No.: PCT/KR2015/009197
§ 371 (c)(1),
(2) Date: Feb. 15, 2018

(87) PCT Pub. No.: WO2017/030229
PCT Pub. Date: Feb. 23, 2017

(65) Prior Publication Data
US 2018/0232063 A1 Aug. 16, 2018

(30) Foreign Application Priority Data
Aug. 19, 2015 (KR) .................. 10-2015-0116768

(51) Int. Cl.
*G06F 3/033* (2013.01)
*A61B 5/00* (2006.01)
(Continued)

(52) U.S. Cl.
CPC .............. *G06F 3/033* (2013.01); *A61B 5/681* (2013.01); *A61B 5/7475* (2013.01); *G06F 1/163* (2013.01); *G06F 1/1694* (2013.01); *G06F 3/016* (2013.01); *G06F 3/038* (2013.01); *G06F 3/0346* (2013.01); *G06F 3/0412* (2013.01); *G06F 3/0414* (2013.01); *G06F 3/0416* (2013.01); *G06F 3/04883* (2013.01); *G06F 3/044* (2013.01); *G06F 2203/04105* (2013.01)

(58) Field of Classification Search
None
See application file for complete search history.

(56) References Cited

U.S. PATENT DOCUMENTS

2010/0079508 A1 4/2010 Hodge et al.
2013/0002538 A1 1/2013 Mooring et al.
(Continued)

FOREIGN PATENT DOCUMENTS

EP 2827226 1/2015
KR 1020150010087 1/2015
(Continued)

OTHER PUBLICATIONS

PCT International Application No. PCT/KR2015/009197, International Search Report dated May 20, 2016, 2 pages.
(Continued)

*Primary Examiner* — Gustavo Polo
(74) *Attorney, Agent, or Firm* — Lee, Hong, Degerman, Kang & Waimey

(57) ABSTRACT

A watch-type mobile terminal is provided that includes a touch screen through which information can be input and output; a force sensor for detecting the strength of force applied to the touch screen by a gesture; an acceleration sensor for detecting the orientation of the terminal; and a control unit which performs control so as to determine whether to activate a screen of the terminal and adjust the touch sensitivity for the touch screen of the terminal according to the orientation of the screen of the terminal.

19 Claims, 23 Drawing Sheets

(51) Int. Cl.
 *G06F 3/038* (2013.01)
 *G06F 3/0346* (2013.01)
 *G06F 1/16* (2006.01)
 *G06F 3/0488* (2013.01)
 *G06F 3/041* (2006.01)
 *G06F 3/01* (2006.01)
 *G06F 3/044* (2006.01)

(56) References Cited

U.S. PATENT DOCUMENTS

| | | |
|---|---|---|
| 2013/0135198 A1 | 5/2013 | Hodge et al. |
| 2014/0132508 A1 | 5/2014 | Hodge et al. |
| 2014/0143737 A1 | 5/2014 | Mistry et al. |
| 2015/0022438 A1 | 1/2015 | Hong |
| 2015/0185837 A1 | 7/2015 | Whitney et al. |
| 2017/0011210 A1* | 1/2017 | Cheong ............... A61B 5/0022 |

FOREIGN PATENT DOCUMENTS

| | | |
|---|---|---|
| KR | 1020150016683 | 2/2015 |
| KR | 1020150068330 | 6/2015 |

OTHER PUBLICATIONS

European Patent Office Application Serial No. 15901769.8, Search Report dated Feb. 21, 2019, 13 pages.

\* cited by examiner (a)

(b)

(a)

(b)

(a)

(b)

(a)

(b)

(a)

(b)

(c)

(d)

(e)

WATCH-TYPE MOBILE TERMINAL

CROSS-REFERENCE TO RELATED APPLICATIONS

This application is the National Stage filing under 35 U.S.C. 371 of International Application No. PCT/KR2015/009197, filed on Sep. 1, 2015, which claims the benefit of earlier filing date and right of priority to Korean Application No. 10-2015-0116768, filed on Aug. 19, 2015, the contents of which are all hereby incorporated by reference herein in their entirety.

TECHNICAL FIELD

The present invention relates to a watch-type mobile terminal having improved reliability by preventing a false operation.

BACKGROUND ART

Terminals may be generally classified as mobile/portable terminals or stationary terminals according to their mobility. Mobile terminals may also be classified as handheld terminals or vehicle mounted terminals according to whether or not a user can directly carry the terminal.

Mobile terminals have become increasingly more functional. Examples of such functions include data and voice communications, capturing images and video via a camera, recording audio, playing music files via a speaker system, and displaying images and video on a display. Some mobile terminals include additional functionality which supports game playing, while other terminals are configured as multimedia players. More recently, mobile terminals have been configured to receive broadcast and multicast signals which permit viewing of content such as videos and television programs.

The mobile terminals are mostly held in the hands and are used by a user, and furthermore, may be expanded to wearable devices which may be worn on the body of the user. Examples of such a wearable device include a watch-type mobile terminal, a glass-type mobile terminal, a head mounted display (HMD), and the like.

Among the mobile terminals, the watch-type mobile terminal is a mobile terminal in which an electronic function, a communication function, a multimedia function, and the like are added to a watch always worn by people. Since the watch-type mobile terminal does not cause negative feeling to people, it appears that the market for the watch-type mobile terminal is explosively created in the future.

Therefore, a research, a development, and commercialization of the watch-type mobile terminal are actively conducted.

In the watch-type mobile terminal, a screen may be turned on/off or an application may be selected and/or executed in response to a touch gesture on the screen.

However, since the watch-type mobile terminal has large touch sensitivity on the screen, false operations, in which the screen is turned on or the application is executed, may often occur regardless of user's intentions. For example, when a user shakes or moves arms, the screen of the watch-type mobile terminal may contact a collar or a body of the user. As a result, the screen of the watch-type mobile terminal may be turned on regardless of user's intentions.

Such a touch false operation may lower reliability of the watch-type mobile terminal to lower a purchasing desire for the watch-type mobile terminal, thereby causing contraction of the market of the watch-type mobile terminal.

DISCLOSURE OF THE INVENTION

Technical Problem

Accordingly, an object of the present invention is to address the above-noted and other problems.

Embodiments of the present invention are directed to provide a watch-type mobile terminal having improved reliability by preventing a false operation.

Technical Solution

In one embodiment, a watch-type mobile terminal includes: a touch screen through which information is input/output; a force sensor configured to sense force intensity applied to the touch screen; an acceleration sensor configured to sense directivity of the watch-type mobile terminal; and a controller configured to determine whether to activate a screen of the watch-type mobile terminal according to the directivity faced by the touch screen of the watch-type mobile terminal and perform control to adjust touch sensitivity on the touch screen of the watch-type mobile terminal.

Advantageous Effects

Effects of a watch-type mobile terminal according to the present invention will be described as follows.

According to at least one of embodiments of the present invention, in a case where a screen of the watch-type mobile terminal is inactivate not to face eyes of a user and a touch gesture is input to activate the activated screen, only when a touch gesture having force intensity greater than or equal to a critical value, the screen may be activated, thereby improving reliability of a product by preventing a false operation in which the screen is activated by a touch regardless of user's intention.

In addition, according to at least one of embodiments of the present invention, when the screen of the watch-type mobile terminal does not face eyes of the user, the screen may be inactivated to prevent a power waste caused by unnecessary power supply.

Furthermore, according to at least one of embodiments of the present invention, although a gesture of allowing the screen of the watch-type mobile terminal to face eyes of the user is input, when acceleration of the watch-type mobile terminal is less than or equal to a critical value, the screen may not be activated, thereby preventing the screen from being turned on by a user's gesture of merely shaking arms while working rather than shaking arms to view the screen of the watch-type mobile terminal of the user.

In addition, according to at least one of embodiments of the present invention, even when touch sensitivity on the screen is large, force intensity may be considered, thereby preventing a false operation, in which a specific function or a specific operation is executed by a weak touch gesture regardless of user's intentions.

Furthermore, according to at least one of embodiments of the present invention, although an icon is executed by a touch gesture regardless of user's intention, only when a touch gesture having a level of force intensity greater than or equal to a critical value is forcedly applied to a screen by the user, an icon related to information very important to the user may be executed, thereby preventing the exposure of information important to the user.

In addition, according to at least one of embodiments of the present invention, objects respectively having a plurality of depths may not be sequentially accessed whenever a touch gesture is input, but an object having a specific depth of the plurality of depths may be directly accessed by one touch gesture having force intensity greater than or equal to a preset critical value, thereby improving user convenience.

Furthermore, according to at least one of embodiments of the present invention, since the screen is directly adjustable to have brightness brighter than that of a bright space by inputting one double tap gesture, an additional gesture for adjusting the screen to have brightness desired by the user after turning the screen may not be required to improve user convenience.

In addition, according to at least one of embodiments of the present invention, a degree of information may be differently displayed according to force intensity of a touch gesture, thereby expanding the degrees of freedom for information selection of the user.

Further scope of applicability of the present invention will become apparent from the detailed description given hereinafter. However, it should be understood that the detailed description and specific examples, while indicating preferred embodiments of the invention, are given by illustration only, since various changes and modifications within the spirit and scope of the invention will become apparent to those skilled in the art from this detailed description.

MODE FOR CARRYING OUT THE INVENTION

Description will now be given in detail according to exemplary embodiments disclosed herein, with reference to the accompanying drawings. For the sake of brief description with reference to the drawings, the same or equivalent components may be provided with the same reference numbers, and description thereof will not be repeated. In general, a suffix such as "module" and "unit" may be used to refer to elements or components. Use of such a suffix herein is merely intended to facilitate description of the specification, and the suffix itself is not intended to give any special meaning or function. In the present disclosure, that which is well-known to one of ordinary skill in the relevant art has generally been omitted for the sake of brevity. The accompanying drawings are used to help easily understand various technical features and it should be understood that the embodiments presented herein are not limited by the accompanying drawings. As such, the present disclosure should be construed to extend to any alterations, equivalents and substitutes in addition to those which are particularly set out in the accompanying drawings.

It will be understood that although the terms first, second, etc. may be used herein to describe various elements, these elements should not be limited by these terms. These terms are generally only used to distinguish one element from another.

It will be understood that when an element is referred to as being "connected with" another element, the element can be connected with the other element or intervening elements may also be present. In contrast, when an element is referred to as being "directly connected with" another element, there are no intervening elements present.

A singular representation may include a plural representation unless it represents a definitely different meaning from the context.

Terms such as "include" or "has" are used herein and should be understood that they are intended to indicate an existence of several components, functions or steps, disclosed in the specification, and it is also understood that greater or fewer components, functions, or steps may likewise be utilized.

Figure 1:
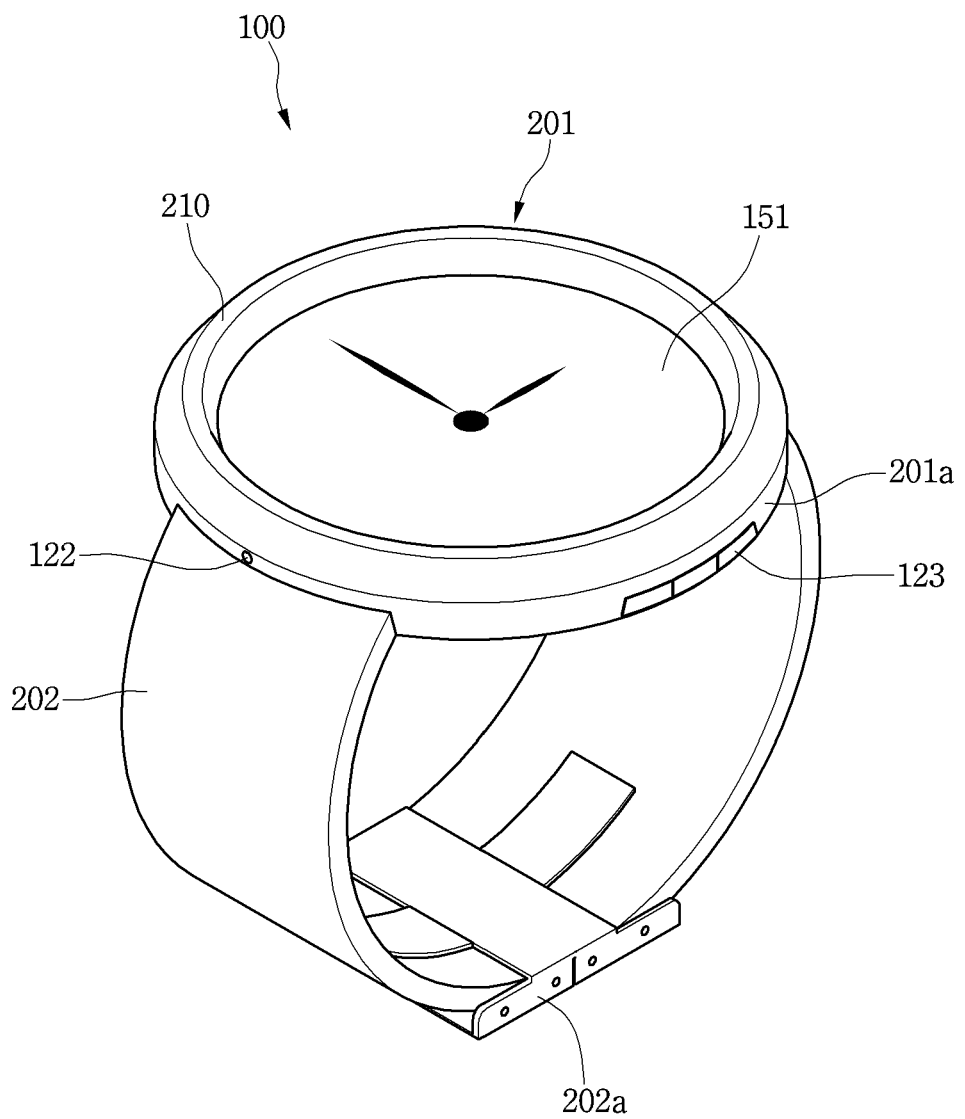
FIG. 1 is a perspective view illustrating one example of a watch-type mobile terminal related to the present invention.

FIG. 1 is a perspective view illustrating one example of a watch-type mobile terminal related to the present invention.

In FIG. 1, a touch screen 151 of a watch-type mobile terminal 100 is different in shape and the functions of other components are the same. That is, the touch screen 151 of the watch-type mobile terminal 100 illustrated in FIG. 1 has a circular shape but is not limited thereto.

The shape of the touch screen 151 of the present invention may include any shape that may provide a visually good expression to a user and assist the user in manipulating the touch screen 151.

Figure 2:
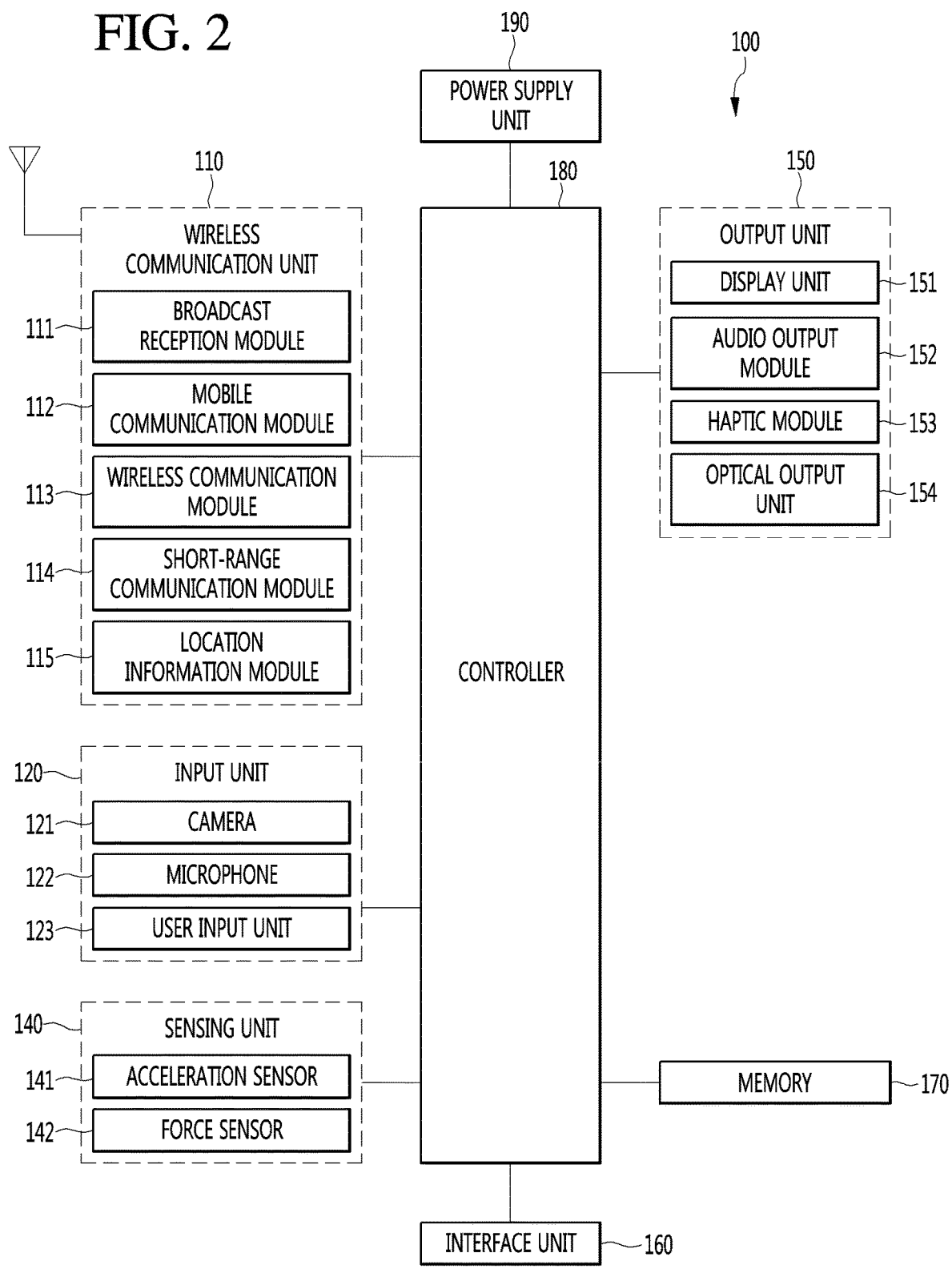
FIG. 2 is a block diagram for explaining a mobile terminal related to the present invention.
Figure 3:
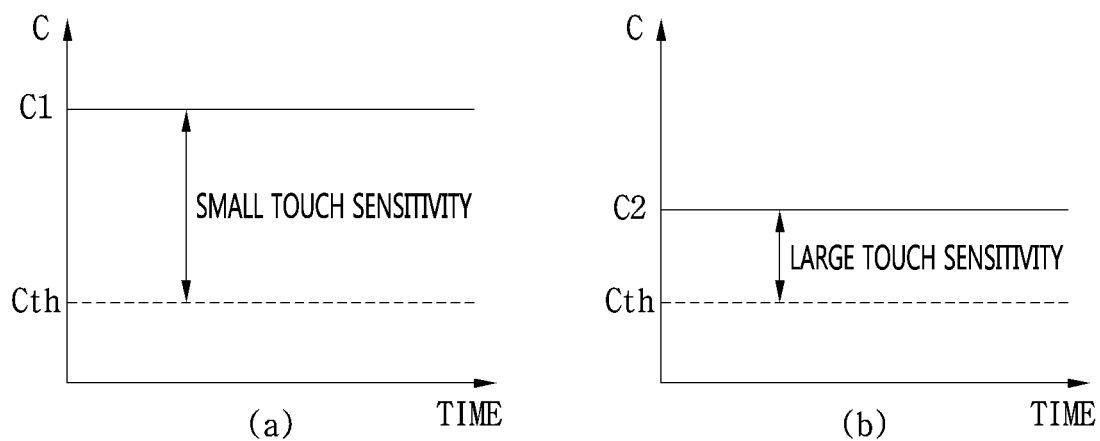
FIG. 3 shows a change in a capacitance value for touch recognition according to whether a metal wheel is mounted.

As illustrated in FIG. 3, the watch-type mobile terminal 100 includes a main body 201 with a display unit 151 and a band 202 connected to the main body 201 to be wearable on a wrist. In general, mobile terminal 100 may be configured to include features that are the same or similar to that of mobile terminal 100 of FIG. 2.

The display unit may be a touch screen on which information is displayed and through which information or a command may be input/output. Unless specified otherwise, the display unit to be described unit later may be a touch screen.

The main body 201 may include a case having a certain appearance. As illustrated, the case may include a first case 201a and a second case 201b cooperatively defining an inner space for accommodating various electronic components. Other configurations are possible. For instance, a single case may alternatively be implemented, with such a case being configured to define the inner space, thereby implementing a mobile terminal 100 with a uni-body.

The watch-type mobile terminal 100 can perform wireless communication, and an antenna for the wireless communication can be installed in the main body 201. The antenna may extend its function using the case. For example, a case including a conductive material may be electrically connected to the antenna to extend a ground area or a radiation area.

The display unit 151 is shown located at the front side of the main body 201 so that displayed information is viewable to a user. In some embodiments, the display unit includes a touch sensor so that the display unit can function as a touch screen.

The main body 201 may include a microphone 122, a user input unit 123, and the like. When the display unit 151 is implemented as a touch screen, the display unit may function as the user input unit 123. Accordingly, a separate key may not be provided in the main body 201. Although not illustrated, the main body 201 may further include an audio output unit and a camera.

The band 202 is commonly worn on the user's wrist and may be made of a flexible material for facilitating wearing of the device. As one example, the band 202 may be made of fur, rubber, silicon, synthetic resin, or the like. The band 202 may also be configured to be detachable from the main body 201. Accordingly, the band 202 may be replaceable with various types of bands according to a user's preference.

In one configuration, the band 202 may be used for extending the performance of the antenna. For example, the band may include therein a ground extending portion (not shown) electrically connected to the antenna to extend a ground area.

The band 202 may include fastener 202a. The fastener 202a may be implemented into a buckle type, a snap-fit hook structure, a Velcro® type, or the like, and include a flexible section or material. The drawing illustrates an example that the fastener 202a is implemented using a buckle.

[Reason for Large Touch Sensitivity]

As described above, since the watch-type mobile terminal 100 has large touch sensitivity on the screen, an undesired false operation frequently occurs.

The reason for the aforementioned large touch sensitivity on the screen of the watch-type mobile terminal will be described.

A metal wheel 210 may be mounted along an edge of the watch-type mobile terminal 100. The metal wheel 210 is made of a metal. When the metal wheel 210 contacts hands of a user or an external conductive member, a current flow occurs. A capacitance value may be decreased by the current flow. Since the decreased capacitance value is near a critical value, a difference between the decreased capacitance value and the critical value is small. Accordingly, touch sensitivity on the screen becomes large.

As illustrated in FIG. 3A, in the watch-type mobile terminal 100 not mounted with the metal wheel 210, since there is no current flow caused by the metal wheel 210, a capacitance value C1 for recognizing a touch is relatively large and a difference between the capacitance value C1 and a critical value Cth is large. Accordingly, touch sensitivity on the screen becomes small. Therefore, in the watch-type mobile terminal 100 not mounted with the metal wheel 210, since touch sensitivity on the screen is small low, although the watch-type mobile terminal 100 contacts a collar or a body of a user due to a user's gesture of shaking or moving arms, a false operation, in which the screen of the watch-type mobile terminal 100 is turned on or an application is executed, does not occur.

On the contrary, as illustrated in FIG. 3B, in the watch-type mobile terminal 100 according to the present invention, mounted with the metal wheel 210, since a current flow occurs due to the metal wheel 210, a capacitance value C2 for recognizing a touch is lowered to be near the critical value Cth. Accordingly, since a difference between the capacitance value C2 and a critical value Cth is small, touch sensitivity on the screen becomes large. Therefore, in the watch-type mobile terminal 100 according to the present invention, due to the large touch sensitivity on the screen, in a case where the watch-type mobile terminal 100 contacts a collar or a body of a user due to a user's gesture of shaking or moving arms, a false operation, in which the screen of the watch-type mobile terminal 100 is turned on or an application is executed, may occur regardless of user's intentions.

The present invention proposes a method of preventing the occurrence of a false operation, in which a screen is turned on or an application is executed by any touch operation except for a touch operation intended by a user when touch sensitivity on the screen is large.

Reference is now made to FIG. 2, where FIG. 2 is a block diagram of a mobile terminal in accordance with the present disclosure.

The watch-type mobile terminal 100 is shown having components such as a wireless communication unit 110, an input unit 120, a sensing unit 140, an output unit 150, an interface unit 160, a memory 170, a controller 180, and a power supply unit 190. It is understood that implementing all of the illustrated components is not a requirement, and that greater or fewer components may alternatively be implemented. Referring now to FIG. 1, the mobile terminal 100 is shown having wireless communication unit 110 configured with several commonly implemented components. For instance, the wireless communication unit 110 typically includes one or more components which permit wireless communication between the mobile terminal 100 and a wireless communication system or network within which the mobile terminal is located.

The wireless communication unit 110 typically includes one or more modules which permit communications such as wireless communications between the mobile terminal 100 and a wireless communication system, communications between the mobile terminal 100 and another mobile terminal, communications between the mobile terminal 100 and an external server. Further, the wireless communication unit 110 typically includes one or more modules which connect the watch-type mobile terminal 100 to one or more networks.

To facilitate such communications, the wireless communication unit 110 includes one or more of a broadcast receiving module 111, a mobile communication module 112, a wireless Internet module 113, a short-range communication module 114, and a location information module 115.

The input unit 120 includes a camera 121 for obtaining images or video, a microphone 122, which is one type of audio input device for inputting an audio signal, and a user input unit 123 (for example, a touch key, a push key, a mechanical key, a soft key, and the like) for allowing a user to input information. Data (for example, audio, video, image, and the like) is obtained by the input unit 120 and may be analyzed and processed by controller 180 according to device parameters, user commands, and combinations thereof.

The sensing unit 140 is typically implemented using one or more sensors configured to sense internal information of the mobile terminal, the surrounding environment of the mobile terminal, user information, and the like. For example, in FIG. 1A, the sensing unit 140 is shown having a proximity sensor 141 and an illumination sensor 142. If desired, the sensing unit 140 may alternatively or additionally include other types of sensors or devices, such as a touch sensor, an acceleration sensor, a magnetic sensor, a G-sensor, a gyroscope sensor, a motion sensor, an RGB sensor, an infrared (IR) sensor, a finger scan sensor, a ultrasonic sensor, an optical sensor (for example, camera 121), a microphone 122, a battery gauge, an environment sensor (for example, a barometer, a hygrometer, a thermometer, a radiation detection sensor, a thermal sensor, and a gas sensor, among others), and a chemical sensor (for example, an electronic nose, a health care sensor, a biometric sensor, and the like), to name a few. The mobile terminal 100 may be configured to utilize information obtained from sensing unit 140, and in particular, information obtained from one or more sensors of the sensing unit 140, and combinations thereof.

The force sensor 142 may be replaced by a pressure sensor but is not limited thereto.

The acceleration sensor 141 according to the present invention may have a function as a virtual gyroscope.

The acceleration sensor 141 may sense directivity of the watch-type mobile terminal 100. The controller 180 may confirm whether the screen of the watch-type mobile terminal 100 faces eyes of a user through the sensing.

Figure 4:
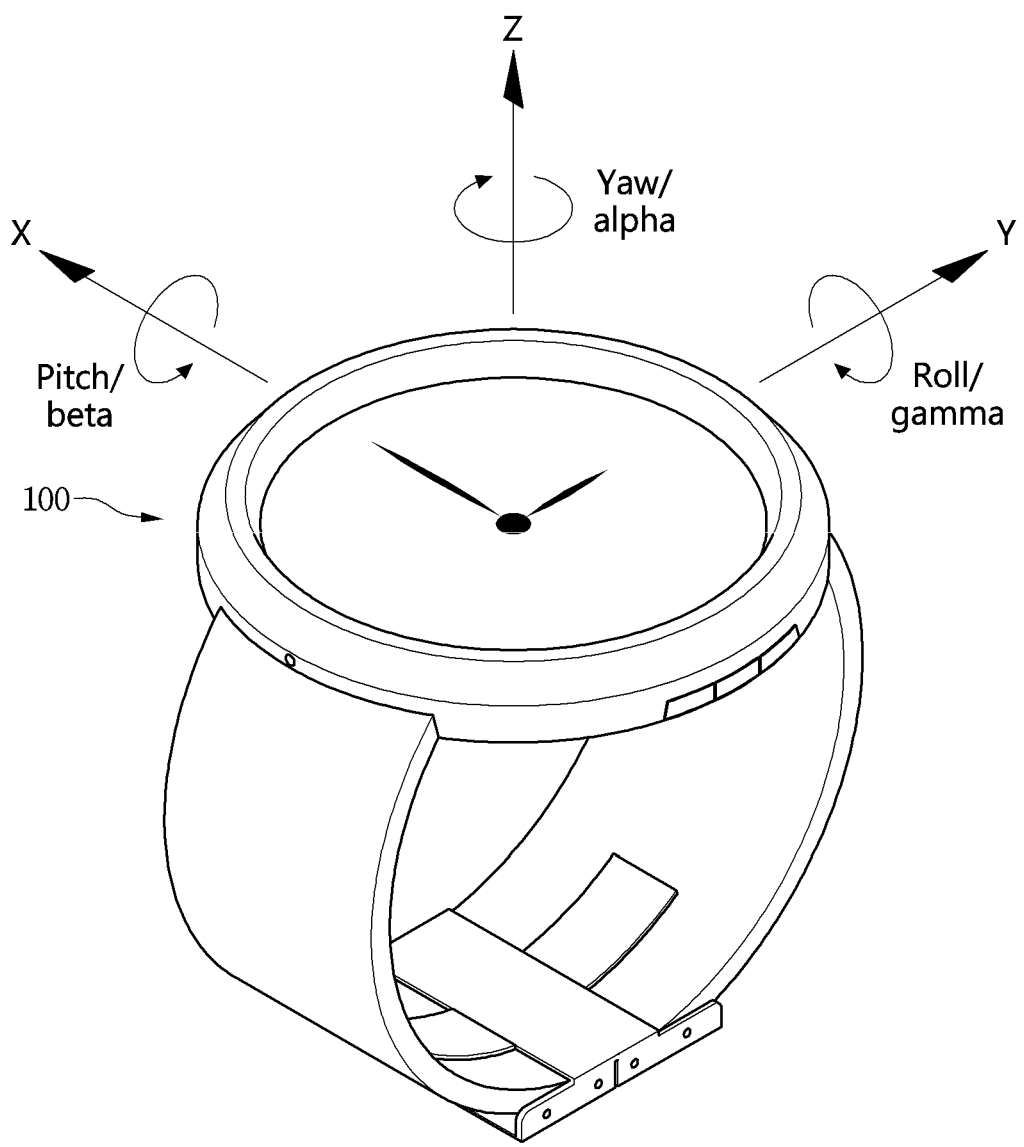
FIG. 4 is a diagram illustrating a Yaw value, a Pitch value, and a Roll value sensed by an acceleration sensor.

As illustrated in FIG. 4, when the acceleration sensor 141 is mounted in the watch-type mobile terminal 100 according to the present invention and the watch-type mobile terminal 100 is divided according to three axes (i.e., an X-axis, a Y-axis, and a Z-axis) perpendicular to one another, the acceleration sensor 141 may sense a degree of rotation on each of the X-axis, the Y-axis, and the Z-axis. Here, Yaw (Alpha) may indicate a direction of rotation on the Z-axis, Pitch (Beta) may indicate a direction of rotation on the X-axis, and Roll (Gamma) may indicate a direction of rotation on the Y-axis.

A direction faced by the watch-type mobile terminal 100 may be grasped based on Yaw (Alpha), Pitch (Beta), and Roll (Gamma), sensed by the acceleration sensor 141.

For example, it may be grasped whether the touch screen 151 of the watch-type mobile terminal 100 faces a face or eyes of a user or other directions.

In the present invention, different UI/UX functions may be implemented according to whether the touch screen 151 of the watch-type mobile terminal 100 faces a face or eyes of a user or other directions. This will be described in detail later.

The force sensor 142 may sense a degree of force applied to the touch screen 151 of the watch-type mobile terminal 100 from a user.

In the present invention, different UI/UX functions may be implemented according to a degree of force applied to the touch screen 151 of the watch-type mobile terminal 100 from a user. This will be described in detail later.

The output unit 150 is typically configured to output various types of information, such as audio, video, tactile output, and the like. The output unit 150 is shown having a display unit 151, an audio output module 152, a haptic module 153, and an optical output module 154. The display unit 151 may have an inter-layered structure or an integrated structure with a touch sensor in order to facilitate a touch screen. The touch screen may provide an output interface between the mobile terminal 100 and a user, as well as function as the user input unit 123 which provides an input interface between the mobile terminal 100 and the user.

The interface unit 160 serves as an interface with various types of external devices that can be coupled to the mobile terminal 100. The interface unit 160, for example, may include any of wired or wireless ports, external power supply ports, wired or wireless data ports, memory card ports, ports for connecting a device having an identification module, audio input/output (I/O) ports, video I/O ports, earphone ports, and the like. In some cases, the mobile terminal 100 may perform assorted control functions associated with a connected external device, in response to the external device being connected to the interface unit 160.

The memory 170 is typically implemented to store data to support various functions or features of the mobile terminal 100. For instance, the memory 170 may be configured to store application programs executed in the mobile terminal 100, data or instructions for operations of the mobile terminal 100, and the like. Some of these application programs may be downloaded from an external server via wireless communication. Other application programs may be installed within the mobile terminal 100 at time of manufacturing or shipping, which is typically the case for basic functions of the mobile terminal 100 (for example, receiving a call, placing a call, receiving a message, sending a message, and the like). It is common for application programs to be stored in the memory 170, installed in the mobile terminal 100, and executed by the controller 180 to perform an operation (or function) for the mobile terminal 100.

The controller 180 typically functions to control overall operation of the mobile terminal 100, in addition to the operations associated with the application programs. The controller 180 may provide or process information or functions appropriate for a user by processing signals, data, information and the like, which are input or output by the various components depicted in FIG. 2, or activating application programs stored in the memory 170.

As one example, the controller 180 controls some or all of the components illustrated in FIG. 2 according to the execution of an application program that have been stored in the memory 170.

The power supply unit 190 can be configured to receive external power or provide internal power in order to supply appropriate power required for operating elements and components included in the mobile terminal 100. The power supply unit 190 may include a battery, and the battery may be configured to be embedded in the terminal body, or configured to be detachable from the terminal body.

At least some of the above components may operate in a cooperating manner, so as to implement an operation, control, or a control method of the watch-type mobile terminal 100 according to various embodiments to be described later. In addition, the operation, the control, or the control method of the watch-type mobile terminal 100 may be implemented on the watch-type mobile terminal 100 by driving at least one application program stored in the memory 170.

Various embodiments described herein may be implemented in a computer-readable recording medium or a recording medium readable by a device similar to the computer by using, for example, software, hardware, or a combination thereof.

Hereinafter, embodiments of a control method performed by the watch-type mobile terminal will be described with reference to the accompanying drawings. It is obvious to those skilled in the art that the present invention is embodied in another specific form within departing from the spirit and essential feature of the present invention.

In the present invention, touch sensitivity on the screen when the screen of the watch-type mobile terminal 100 faces eyes of a user may be set differently from touch sensitivity on the screen when the screen of the watch-type mobile terminal 100 does not face eyes of the user. For example, the touch sensitivity on the screen when the screen of the watch-type mobile terminal 100 does not face eyes of the user may be set to be lower than the touch sensitivity on the screen when the screen of the watch-type mobile terminal 100 faces eyes of the user.

Except for the case where the screen of the watch-type mobile terminal 100 faces eyes of the user, a case where the screen of the watch-type mobile terminal 100 faces any direction may correspond to the case where the screen of the watch-type mobile terminal 100 does not face eyes of the user. The case where the screen of the watch-type mobile terminal 100 does not face eyes of the user may be a case where the user does not use the watch-type mobile terminal 100, and may indicate a state in which the watch-type mobile terminal 100 is placed on a desk or the watch-type mobile terminal 100 worn on a wrist of the user is shaken according to a movement of the user.

The case where the screen of the watch-type mobile terminal 100 faces eyes of the user may indicate a case where the user is to use the watch-type mobile terminal 100. Various functions provided by the watch-type mobile terminal 100 may be executed.

In order to execute desired functions through the watch-type mobile terminal, a user may input a gesture of raising a wrist of the user such that the screen of the watch-type mobile terminal faces eyes of the user, wherein the watch-type mobile terminal 100 is worn on the wrist of the user.

When the screen of the watch-type mobile terminal 100 faces eyes of the user, touch sensitivity on the screen of the watch-type mobile terminal 100 becomes large. In this case, even when a touch gesture is not input on the screen of the watch-type mobile terminal 100, the screen of the watch-type mobile terminal 100 may be activated. Accordingly, the screen may be displayed in a state of being converted from an off-screen to an on-screen. Here, the off-screen may be a first screen, and the on-screen may be a second screen.

The off-screen may be a black screen or an ambient screen, and the on-screen may be a standby screen.

On the contrary, the off-screen may be a black screen, and the on-screen may be an ambient screen or a standby screen.

The watch-type mobile terminal 100 may display the ambient screen or the standby screen to provide information. In addition, the screen of the watch-type mobile terminal 100 may become the black screen on which a display of information is impossible.

Since power is not applied to a screen implemented using a display unit such as an LCD or an OLED, any information may not be displayed on the black screen. In information including an object and a background region, the object is displayed on the ambient screen, but the background region corresponds to a black gradation and is not displayed on the ambient screen. The object as well as the background region may be displayed on the standby screen.

As described above, since the background region is not displayed on the ambient screen, power is not applied to the background region. Accordingly, power consumption in the ambient screen may be reduced compared to the standby screen.

Commonly, when a touch gesture is not input on the standby screen for a certain period of time, the standby screen may be converted into the ambient screen. Here, the standby screen may be a first screen, and the ambient screen may be a second screen.

When a power-off command is input to the standby screen or the ambient screen, the standby screen or the ambient screen may be converted into the black screen.

Figure 5:
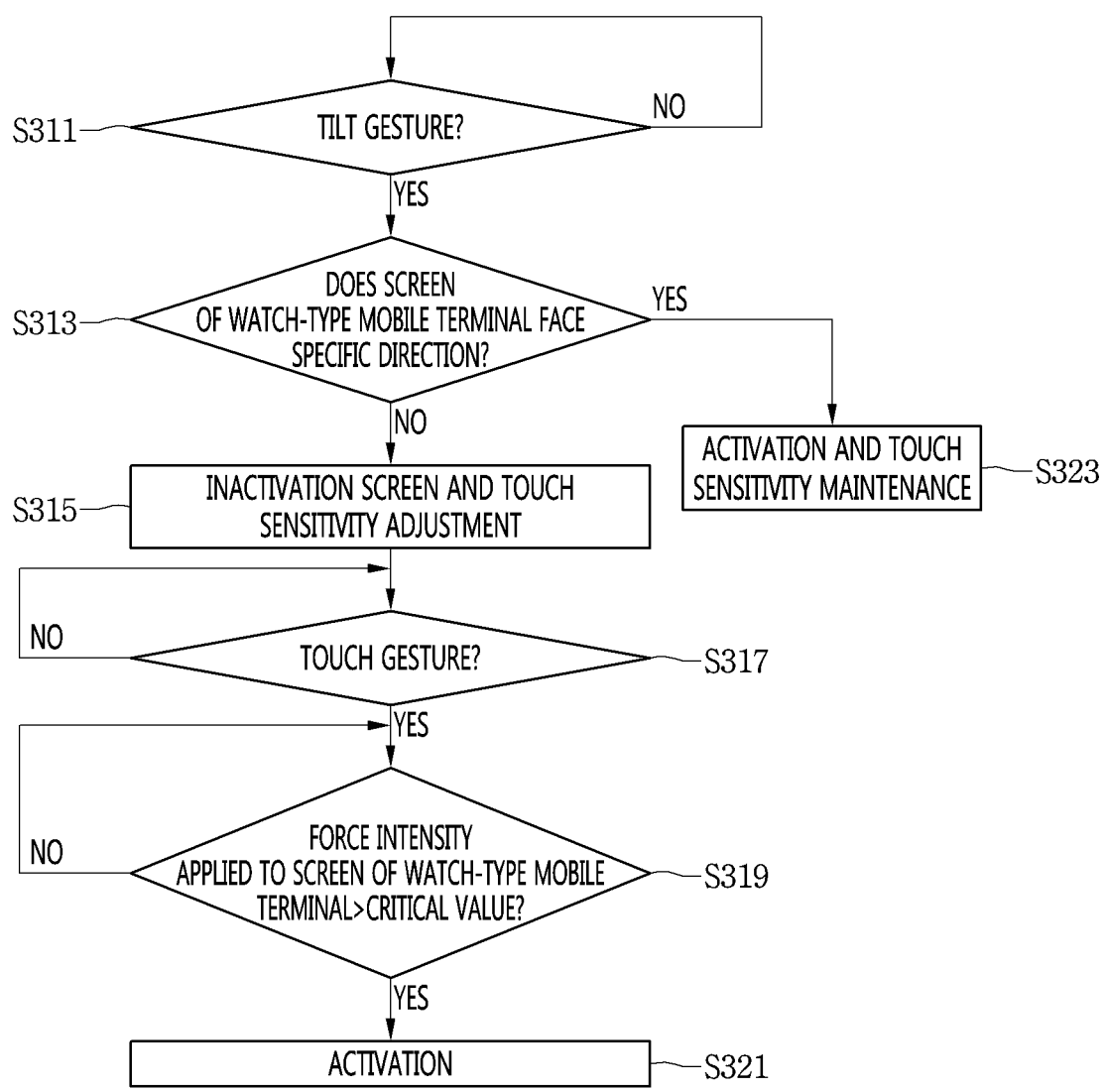
FIG. 5 is a flowchart illustrating a method of controlling a watch-type mobile terminal, according to a first embodiment of the present invention.

FIG. 5 is a flowchart illustrating a method of controlling the watch-type mobile terminal, according to a first embodiment of the present invention.

Referring to FIGS. 2 and 5, the controller 180 may confirm whether a tilt gesture is input (S311).

The tilt gesture may be sensed by the acceleration sensor 141. The tilt gesture may be a gesture of raising a hand of a user, facing a downward direction, or twisting a wrist of the user in a clockwise direction or an anticlockwise direction, the user wearing the watch-type mobile terminal. However, the present invention is not limited thereto.

When the tilt gesture is input, the controller 180 may confirm whether the screen of the watch-type mobile terminal 100 faces a specific direction (S313).

As illustrated in FIG. 4, the acceleration sensor 141 may obtain a Yaw value, a Pitch value, and a Roll value. The controller 180 may confirm based on the obtained Yaw, Pitch, and Roll values whether the screen of the watch-type mobile terminal 100 faces the specific direction.

Here, the specific direction may be a direction in which the screen of the watch-type mobile terminal 100 faces eyes of the user.

When a gesture of allowing the screen of the watch-type mobile terminal 100 to face the specific direction, i.e., eyes of the user is input, the controller 180 may activate the screen and maintain touch sensitivity on the screen (S323).

The activation of the screen may mean that a black screen is converted into a standby screen or an ambient screen is converted into the standby screen. Here, the black screen or the ambient screen may be a first screen, and the standby screen may be a second screen.

When the screen of the watch-type mobile terminal 100 faces eyes of the user, the screen may be activated although a separate touch gesture is not input from the user.

In another embodiment, when the screen of the watch-type mobile terminal 100 faces eyes of the user, the watch-type mobile terminal 100 may be still inactivated, and touch sensitivity on the screen may be just set to the first critical value Cth1. In this case, the screen may be activated by a touch gesture. That is, when a touch gesture having weak force intensity is input on the screen of the watch-type mobile terminal 100 from a user, the screen may be easily activated because the touch sensitivity on the screen is large. Since touch sensitivity on the screen is set to the first critical value Cth1, the screen may also be easily activated by the touch gesture having weak force intensity.

In the present invention, touch sensitivity on the screen may be changed according to whether the screen of the watch-type mobile terminal 100 faces eyes of the user.

Figure 6:
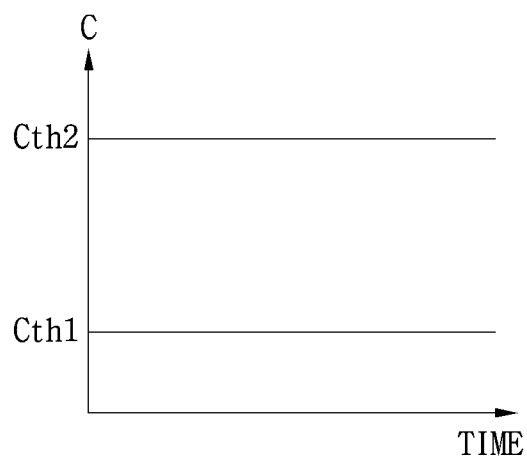
FIG. 6 shows a change in a critical value according to touch sensitivity.

As described above, the change in touch sensitivity on the screen may mean that a critical value is changed as illustrated in FIG. 6, the critical value being a reference value for recognizing a touch.

When the screen of the watch-type mobile terminal 100 faces eyes of the user, touch sensitivity on the screen may be large and may be set to the first critical value Cth1 as illustrated in FIG. 6. Since the first critical value Cth1 is smaller than a second critical value Cth2, touch sensitivity on the screen, corresponding to the first critical value Cth1, may be larger than touch sensitivity on the screen, corresponding to the second critical value Cth2.

Since the first critical value Cth1 itself is small, a capacitance value larger than the first critical value Cth1 may even be obtained by a minute touch of a user on a screen. Thus, the controller 180 recognizes the minute touch as a touch command to execute an operation corresponding to the touch command.

When the screen of the watch-type mobile terminal 100 does not face eyes of the user, touch sensitivity on the screen may be small and may be set to the second critical value Cth2 as illustrated in FIG. 6. Since the second critical value Cth2 is larger than the first critical value Cth1, touch sensitivity on the screen, corresponding to the second critical value Cth2, may be smaller than touch sensitivity on the screen, corresponding to the first critical value Cth1. In this case, the screen is not activated by a touch gesture having weak force intensity, input on the screen of the watch-type mobile terminal 100 from a user. The screen may only be activated when a touch gesture, having force intensity greater than the weak force intensity, is input (see S319 and S321).

Referring to FIGS. 1 and 5, when the screen of the watch-type mobile terminal 100 does not face eyes of the user, the controller 180 may inactivate the screen and may adjust touch sensitivity on the screen.

The inactivation of the screen may mean that a current screen not inactivated is maintained. When the current screen is a black screen, the black screen may be maintained.

The adjustment of touch sensitivity on the screen may be performed by adjusting the preset first critical value Cth1 to the second critical value Cth2 as illustrated in FIG. 6.

The second critical value Cth2 is larger than the first critical value Cth1, which means that touch sensitivity on the screen, corresponding to the second critical value Cth2, is smaller than touch sensitivity on the screen, corresponding to the first critical value Cth1.

As described above, when the first critical value Cth1 is adjusted to the second critical value Cth2, a capacitance value due to a touch of a user on a screen may be smaller than the second critical value Cth2. Thus, a screen may not be just activated by a touch.

In this case, a screen may be activated through force intensity of a touch. Force intensity of a touch on a screen may be sensed by the force sensor 142.

When a touch gesture for activating a screen is input from a user (S317), the controller 180 may confirm whether force intensity, applied on the screen of the watch-type mobile terminal 100 by a touch gesture on the screen of the watch-type mobile terminal 100, is greater than a critical value (S319).

When the force intensity, applied on the screen by the touch gesture, is smaller than the critical value, the screen may be maintained in an inactivated state.

When the force intensity, applied on the screen by the touch gesture, is greater than the critical value, the controller 180 may activate the screen (S321).

The activation of the screen in S321 may be the same as activation of a screen in S323. That is, a black screen may be converted into a standby screen or an ambient screen may be converted into the standby screen by the activation of the screen.

Hereinafter, a screen activating method according to the present invention will be described with reference to the accompanying drawings.

Figure 7:
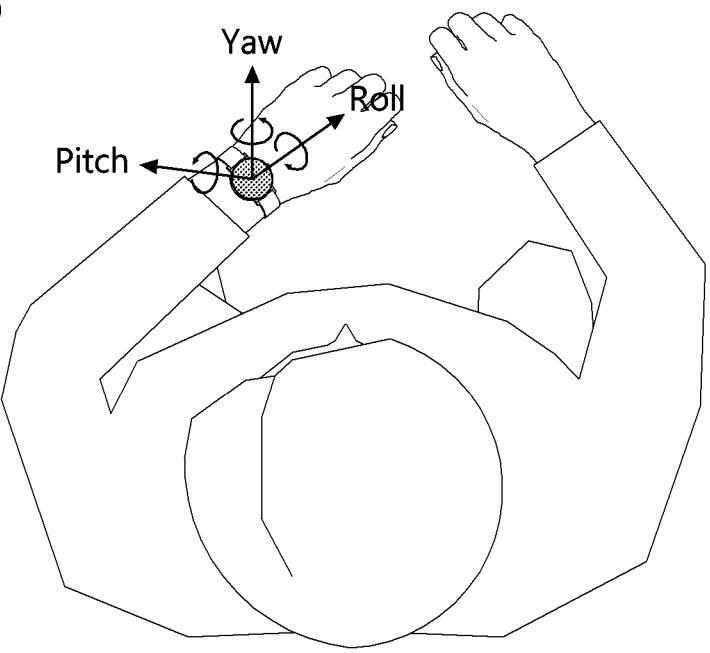
FIG. 7 illustrates exemplary screens showing that a screen is activated by a gesture.
Figure 7:
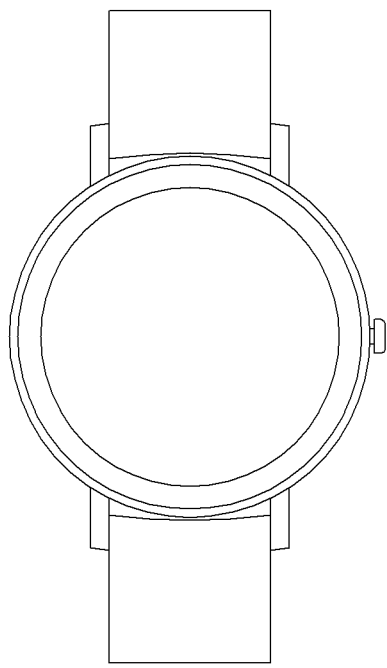

As illustrated in FIG. 7A, in order to use the watch-type mobile terminal 100, when a user raises a user's arm such that the screen of the watch-type mobile terminal 100 faces eyes of the user, as illustrated in FIG. 7B, the screen may be displayed in a state of being activated, for example, a state of being converted from a black screen to a standby screen (see S313 and S323).

Figure 8:
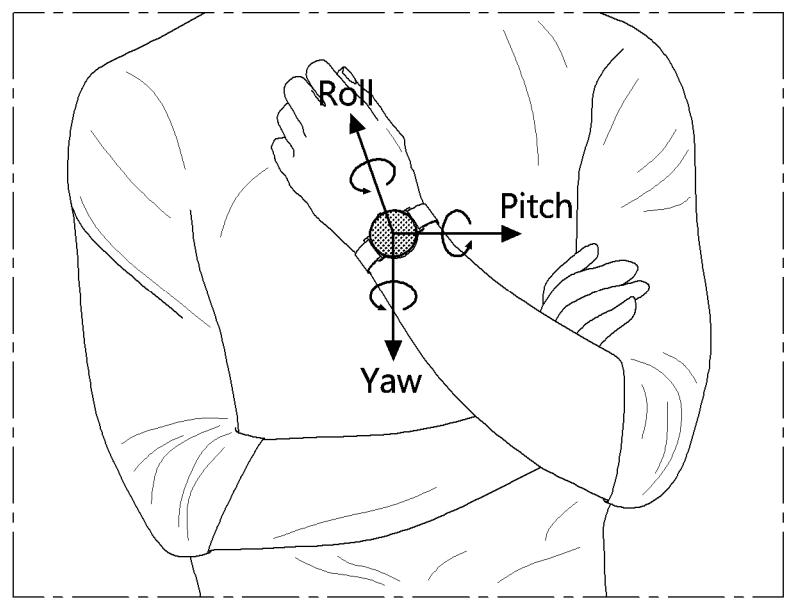
FIG. 8 illustrates exemplary screens showing that a screen is maintained in an inactivated state by a gesture.
Figure 8:
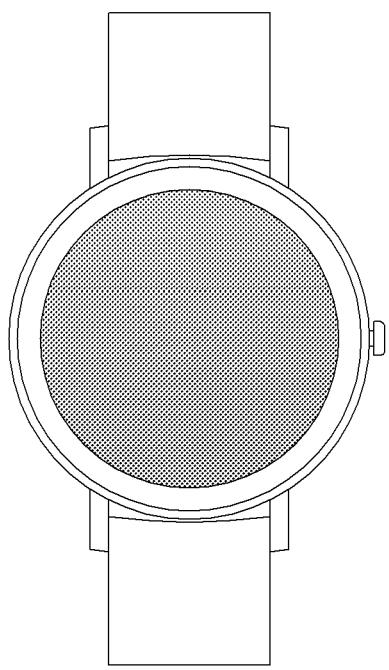

On the contrary, as illustrated in FIG. 8A, when a user does not use the watch-type mobile terminal 100, the screen of the watch-type mobile terminal 100 does not face eyes of the user. In this case, as illustrated in FIG. 8b, the screen may be inactivated, for example, a black screen may be maintained (see S313 and S315).

Figure 9:
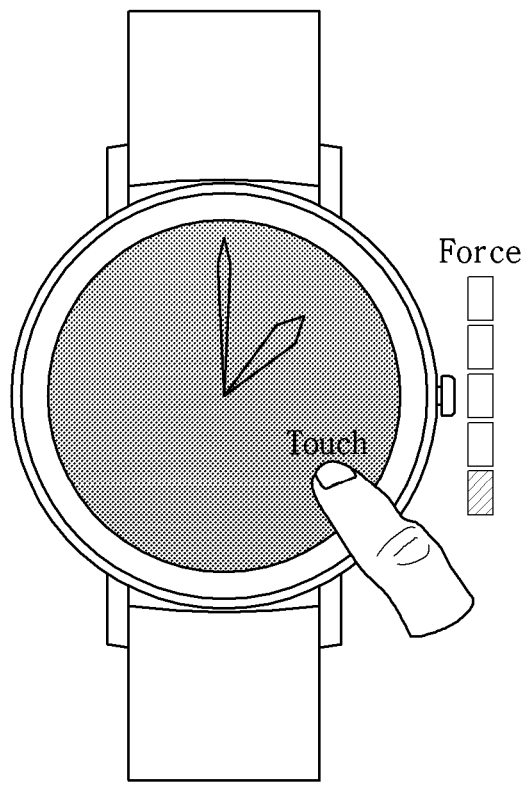
FIG. 9 illustrates exemplary screens showing that a screen is activated when the screen is inactivated by a gesture.
Figure 9:
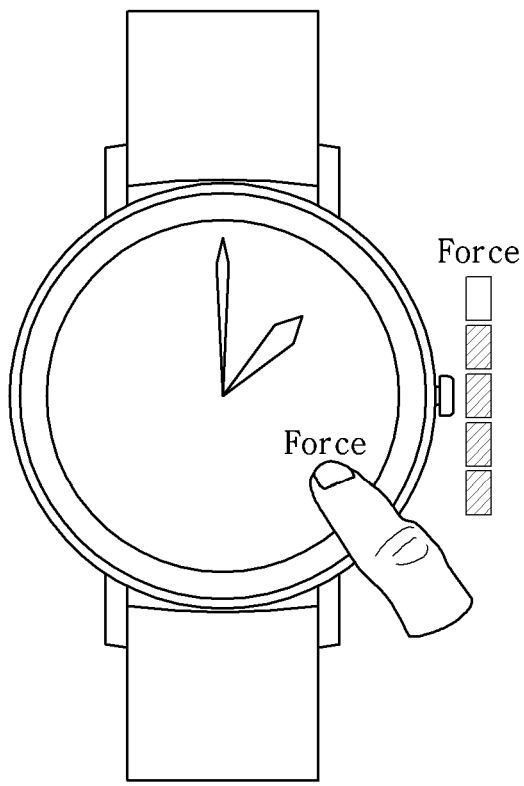

As illustrated in FIG. 9A, when the screen of the watch-type mobile terminal 100 does not face eyes of a user and thus is inactivated, in a case where a touch gesture having weak force intensity is input from the user so as to activate the screen, the screen may be still maintained in an inactivated state.

On the contrary, as illustrated in FIG. 9B, when a touch gesture, having force greater than the weak force intensity and the critical value, is input from a user, the screen may be displayed in a state of being activated, for example, a state of being converted from a black screen to a standby screen (see S319 and S321).

When the screen is activated, and thus, a black screen is converted into a standby screen regardless of user's intentions, although a user does not use the watch-type mobile terminal 100, power may be continuously supplied so as to maintain the standby screen. Thus, a power waste may occur.

According to the present invention, when the screen of the watch-type mobile terminal 100 does not face eyes of a user, the screen may be inactivated to prevent a power waste caused by unnecessary power supply.

When the screen is activated, and thus, a black screen is converted into a standby screen regardless of user's intentions, in a case where an additional touch screen is input with respect to icons displayed on the standby screen, an application, corresponding to an icon, may be unintentionally executed.

According to the present invention, when the screen of the watch-type mobile terminal 100 does not face eyes of a user and thus is inactivated and a touch gesture is input so as to activate the inactivated screen, the screen may only be activated when a touch gesture, having force intensity greater than or equal to a critical value, is input, thereby improving reliability of a product by preventing a false operation in which a screen is activated by a touch regardless of user's intentions.

Figure 10:
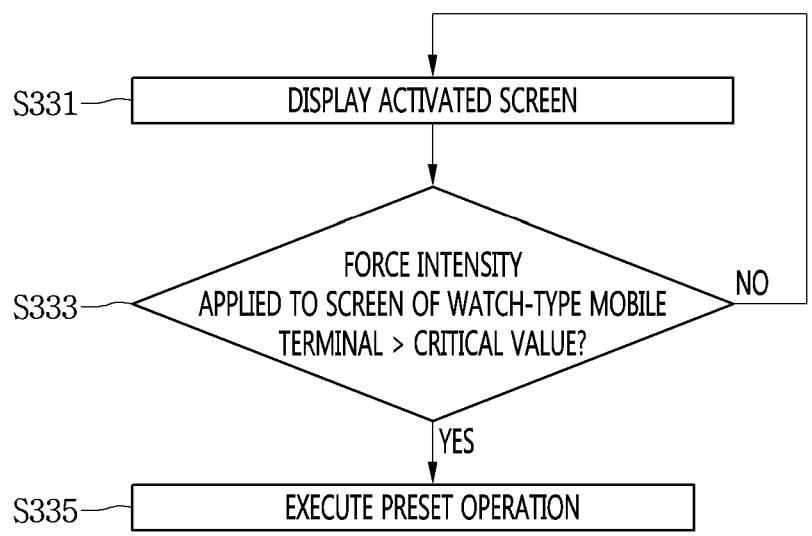
FIG. 10 is a flowchart illustrating a method of controlling a watch-type mobile terminal, according to a second embodiment of the present invention.

FIG. 10 is a flowchart illustrating a method of controlling the watch-type mobile terminal, according to a second embodiment of the present invention.

The second embodiment may include control operations after the screen is activated in S321 or S321 of the first embodiment but is not limited thereto.

Referring to FIGS. 2 and 10, the controller 180 may activate the activated screen (S331).

As described in the first embodiment (see FIG. 5), when a gesture of allowing the screen of the watch-type mobile terminal 100 to face eyes of a user is input (S313) or when force intensity, applied to the screen of the watch-type mobile terminal 100 by a touch gesture on the screen of the watch-type mobile terminal 100, is greater than a critical value in a state in which the screen of the watch-type mobile terminal 100 does not face eyes of the user (S319), an inactivated screen may be converted into an activated screen. In addition, the activated screen may be displayed on the touch screen 151.

The inactivated screen may be, for example, a black screen, and the activated screen may be, for example, an ambient screen or a standby screen, but the present invention is not limited thereto.

When the force intensity, applied to the screen of the watch-type mobile terminal 100 by the touch gesture on the screen of the watch-type mobile terminal 100, is greater than the critical value (S333), the controller 180 may execute a preset operation (S335).

For example, when the preset operation is execution of a notification application and the force intensity is greater than the critical value, the controller 180 may execute the notification application (see FIGS. 12C and 12D).

Figure 11:
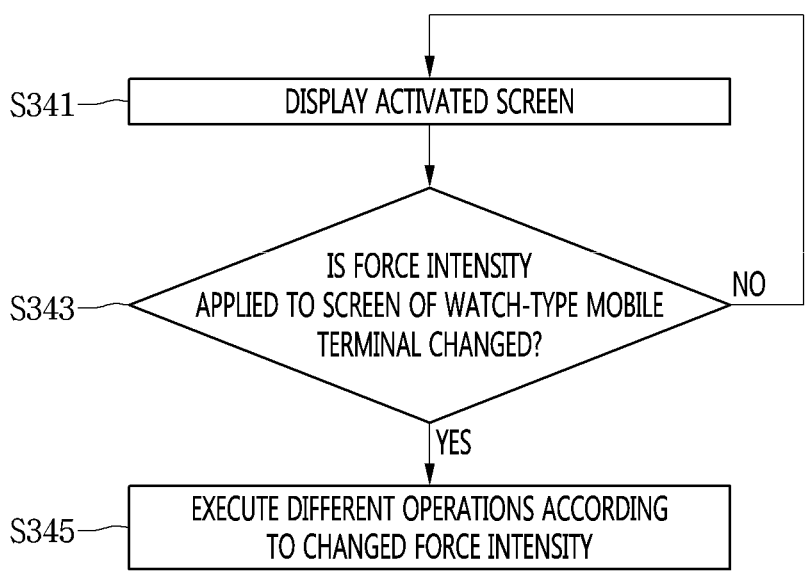
FIG. 11 is a flowchart illustrating a method of controlling a watch-type mobile terminal, according to a third embodiment of the present invention

FIG. 11 is a flowchart illustrating a method of controlling the watch-type mobile terminal, according to a third embodiment of the present invention.

The third embodiment may include control operations after the screen is activated in S321 or S321 of the first embodiment but is not limited thereto.

Referring to FIGS. 2 and 11, the controller 180 may display the activated screen (S341).

As described in the first embodiment (see FIG. 5), when a gesture of allowing the screen of the watch-type mobile terminal 100 to face eyes of a user is input (S313) or when force intensity, applied to the screen of the watch-type mobile terminal 100 by a touch gesture on the screen of the watch-type mobile terminal 100, is greater than a critical value in a state in which the screen of the watch-type mobile terminal 100 does not face eyes of the user (S319), an inactivated screen may be converted into an activated screen. In addition, the activated screen may be displayed on the touch screen 151.

The inactivated screen may be, for example, a black screen, and the activated screen may be, for example, an ambient screen or a standby screen, but the present invention is not limited thereto.

When the force intensity, applied to the screen of the watch-type mobile terminal 100 by the touch gesture on the screen of the watch-type mobile terminal 100, is changed (S343), the controller 180 may execute different operations according to the changed force intensity (S345).

For example, brightness of a screen may be changed according to the changed force intensity. That is, as force intensity is increased, a screen may become brighter. When a first level of force intensity is applied to the screen of the watch-type mobile terminal 100, the screen of the watch-type mobile terminal 100 is adjusted to a screen having a first gradation of brightness. When a second level of force intensity, greater than the first level of force intensity, is applied to the screen of the watch-type mobile terminal 100, the screen of the watch-type mobile terminal 100 is adjusted to a screen having a second gradation of brightness greater than the first gradation.

On the contrary, as force intensity is increased, a screen may become darker.

For example, intensity of a sound may be changed according to the changed force intensity. That is, as force intensity is increased, a sound may be increased. When the first level of force intensity is applied to the screen of the watch-type mobile terminal 100, a sound may be adjusted to a sound having first intensity. When the second level of force intensity, greater than the first level of force intensity, is applied to the screen of the watch-type mobile terminal 100, a sound may be adjusted to a sound having second intensity greater than the first intensity.

On the contrary, as force intensity is increased, a sound may be decreased.

For example, a telephone call connection with respect to different abbreviated numbers may be executed according to the changed force intensity.

For example, a telephone number of a called party "A" may be set to an abbreviated number "1", a telephone number of a called party "B" may be set to an abbreviated number "2", and a telephone number of a called party "C" may be set to an abbreviated number "3". In this case, when the first level of force intensity is applied to the screen of the watch-type mobile terminal 100, a call signal may be transmitted to a phone of the called party "A", corresponding to the abbreviated number "1". When the force intensity of the second level, greater than the first level of force intensity, is applied to the screen of the watch-type mobile terminal 100, a call signal may be transmitted to a phone of the called party "B", corresponding to the abbreviated number "2". When force intensity of a third level, greater than the force intensity of the second level, is applied to the screen of the watch-type mobile terminal 100, a call signal may be transmitted to a phone of the called party "C", corresponding to the abbreviated number "3".

In addition, various functions may be executed according to a change in force intensity applied to the screen of the watch-type mobile terminal 100, and it is obvious that the execution of the various functions not heretofore described is also included within the scope of the technical concept of the present invention.

Hereinafter, methods of activating a screen and executing different operations or functions in various circumstances will be described with reference to FIGS. 12 to 24.

Figure 12:
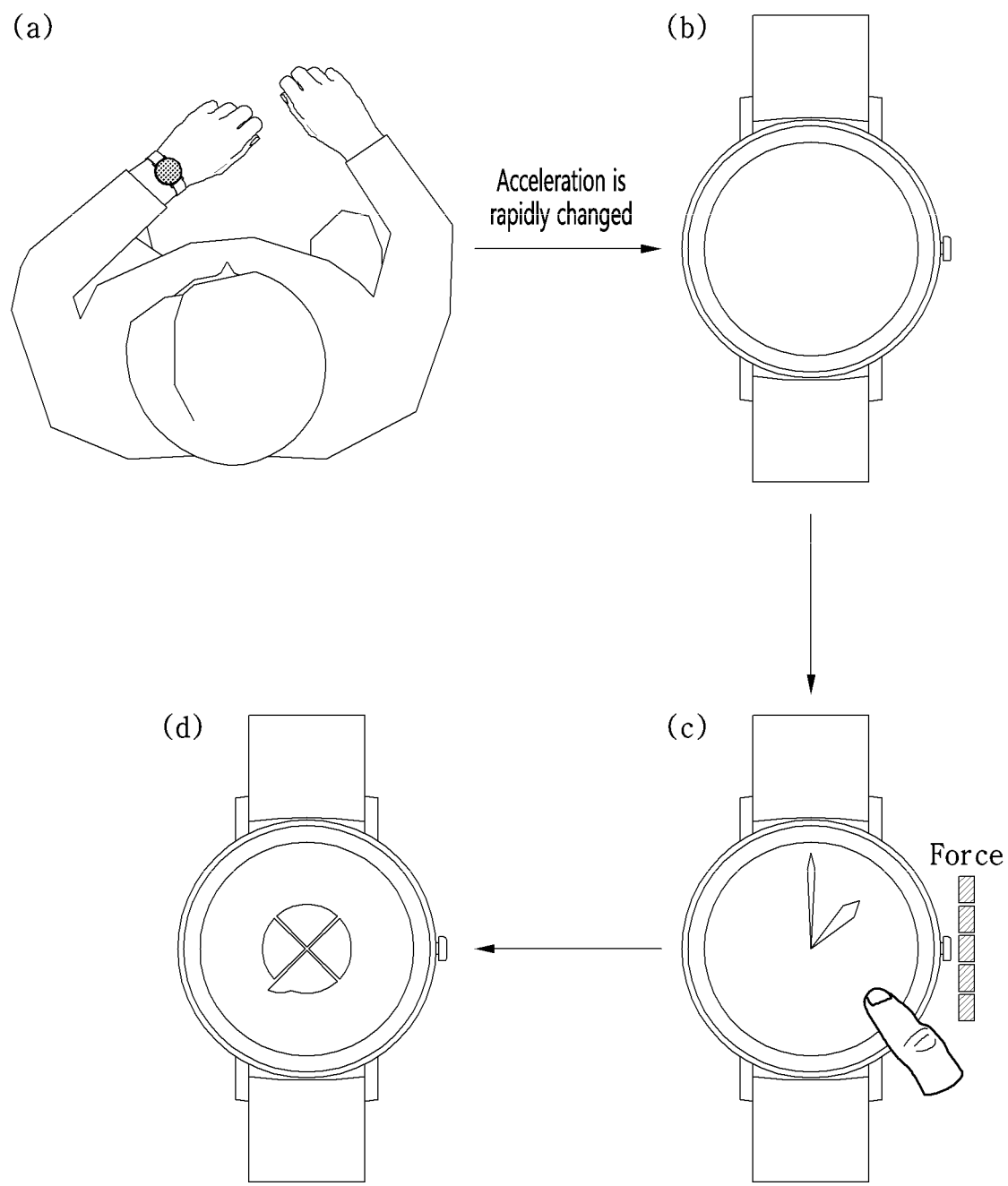
FIG. 12 illustrates exemplary screens showing that a screen is activated or an operation is executed according to acceleration and force intensity of a tilt gesture.

FIG. 12 illustrates exemplary screens showing that a screen is activated or an operation is executed according to acceleration and force intensity of a tilt gesture.

For example, when a tilt gesture is generated such that the watch-type mobile terminal 100 worn on a wrist of a user faces eyes of the user, different functions may be executed according to acceleration of the tilt gesture.

When acceleration of the tilt gesture on the watch-type mobile terminal 100 is rapidly changed, i.e., the acceleration of the tilt gesture is greater than a critical value, as illustrated in FIG. 12A, the screen of the watch-type mobile terminal 100 may be activated, and thus, a black screen may be converted into an ambient screen or a standby screen, as illustrated in FIG. 12B. Here, the black screen may be a first screen, and the ambient screen or the standby screen may be a second screen.

The rapidness of the acceleration of the tilt gesture may be determined based on a Yaw value, a Pitch value, and a Roll value obtained from the acceleration sensor 141.

The rapidness of the acceleration of the tilt gesture may be determined based on a degree in which each of the Yaw value, the Pitch value, and the Roll value obtained from the acceleration sensor 141 is changed for a given period of time.

As illustrated in FIG. 12C, when a touch gesture having force intensity greater than or equal to a critical value is input on the ambient screen or the standby screen, a preset specific operation may be executed.

For example, as illustrated in FIG. 12D, when the touch gesture having the force intensity greater than or equal to the critical value is input on the ambient screen or the standby screen, a notification application may be executed.

Figure 13:
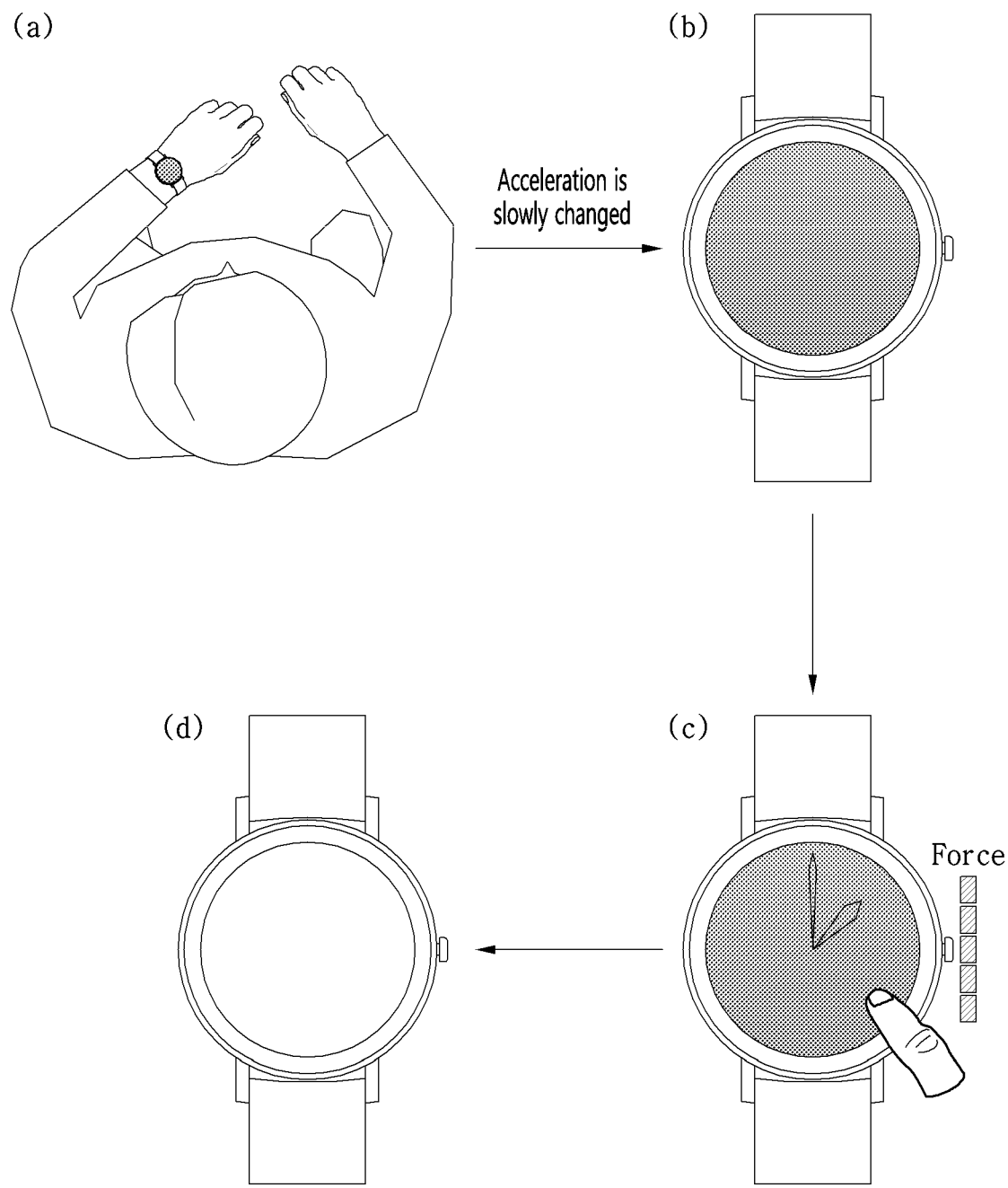
FIG. 13 illustrates other exemplary screens showing that a screen is activated or an operation is executed according to acceleration and force intensity of a tilt gesture.

FIG. 13 illustrates other exemplary screens showing that a screen is activated or an operation is executed according to acceleration and force intensity of a tilt gesture.

Unlike FIG. 12, acceleration of a tilt gesture is slowly changed in FIG. 13.

When acceleration of a tilt gesture on the watch-type mobile terminal 100 is slowly changed, i.e., the acceleration of the tilt gesture is smaller than a critical value, as illustrated in FIG. 13A, the screen of the watch-type mobile terminal 100 may not be activated, and thus, a current black screen may be maintained as illustrated in FIG. 13B.

In this case, when a touch gesture (first touch gesture) having force intensity greater than or equal to a critical value is input on an ambient screen or a standby screen, as illustrated in FIG. 13C, the screen of the watch-type mobile terminal 100 may be activated, and thus, a black screen may be converted into the ambient screen or the standby screen, as illustrated in FIG. 13D.

Although not illustrated, when a touch gesture (second touch gesture) having certain force intensity or more is input on an ambient screen or a standby screen, a specific function, such as an notification application, may be executed.

Force intensity of the second touch gesture may be equal to or greater than force intensity of the first touch gesture, but the present invention is not limited thereto.

As described in FIGS. 12 and 13, although a gesture of allowing the screen of the watch-type mobile terminal 100 to face eyes of a user is input, when acceleration of the watch-type mobile terminal 100 is less than or equal to a critical value, the screen may not be activated, thereby preventing the screen from being turned on by a user's gesture of merely shaking arms while working rather than shaking arms to view the screen of the watch-type mobile terminal 100 of the user.

Figure 14:
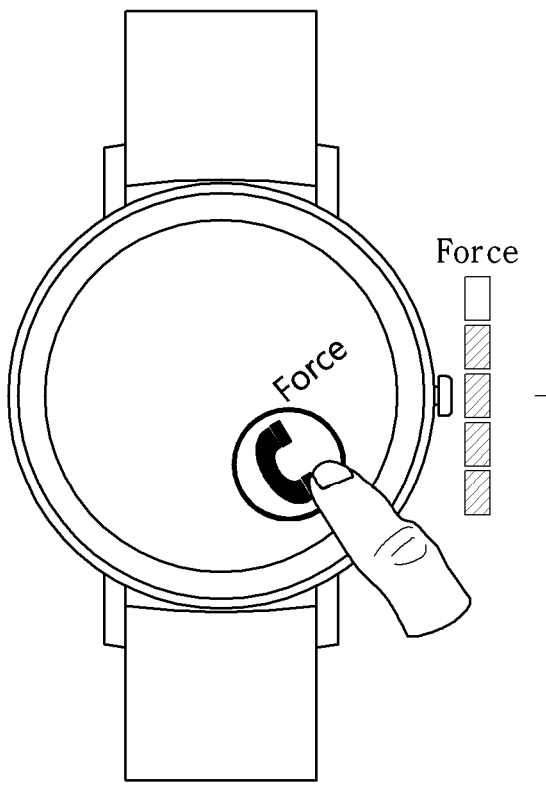
FIG. 14 illustrates exemplary screens showing that a specific application is executed when certain force intensity is applied to a screen in a turn-on state of the screen.
Figure 14:
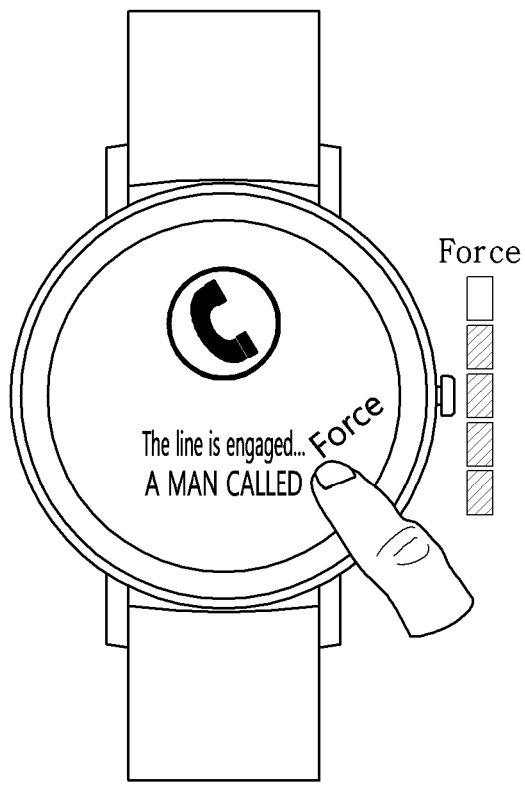

FIG. 14 illustrates exemplary screens showing that a specific application is executed when certain force intensity is applied to a screen in a turn-on state of the screen.

As illustrated in FIG. 14A, a screen may be activated and thus be displayed in a state of being converted from a black screen to an ambient screen or a standby screen.

Icons capable of executing various applications may be displayed on the ambient screen or the ambient screen.

When sensitivity on the screen is large, an application corresponding to a specific icon may be executed by a touch gesture not intended by a user.

The execution of the application may include dialing, transmission of a text, transmission of email, and the like.

For example, in a case where a telephone call connection icon with respect to a specific called party is displayed on the screen, even when a user weakly touches the telephone call connection icon out of awareness, despite not intending call, a call signal may be transmitted to a phone of the specific called party.

Therefore, when the screen enters an activated state, a specific icon may be set so as not to be just executed by a touch gesture. That is, it may be determined whether to execute a specific icon, taking into account a touch gesture as well as a level of force intensity applied to a screen due to the touch gesture.

As illustrated in FIG. 14B, in a case where a specific level of force intensity is set as a critical value, only when a level of force intensity applied to a screen is greater than or equal to the critical value, a specific icon may be executed.

In a case where force intensity is not considered, when touch sensitivity on the screen is set to a large value, a false operation, in which a corresponding icon is also executed by a weak touch gesture, may occur regardless of user's intentions.

However, in a case where force intensity is considered, even when touch sensitivity on the screen is large, a specific icon is not executed by a weak touch gesture regardless of user's intentions. This is because force intensity of the weak touch gesture is less than or equal to a preset critical value.

Therefore, according to the present invention, even when touch sensitivity on the screen is large, force intensity may be considered, thereby preventing a false operation, in which a specific function or a specific operation is executed by a weak touch gesture regardless of user's intentions.

Figure 15:
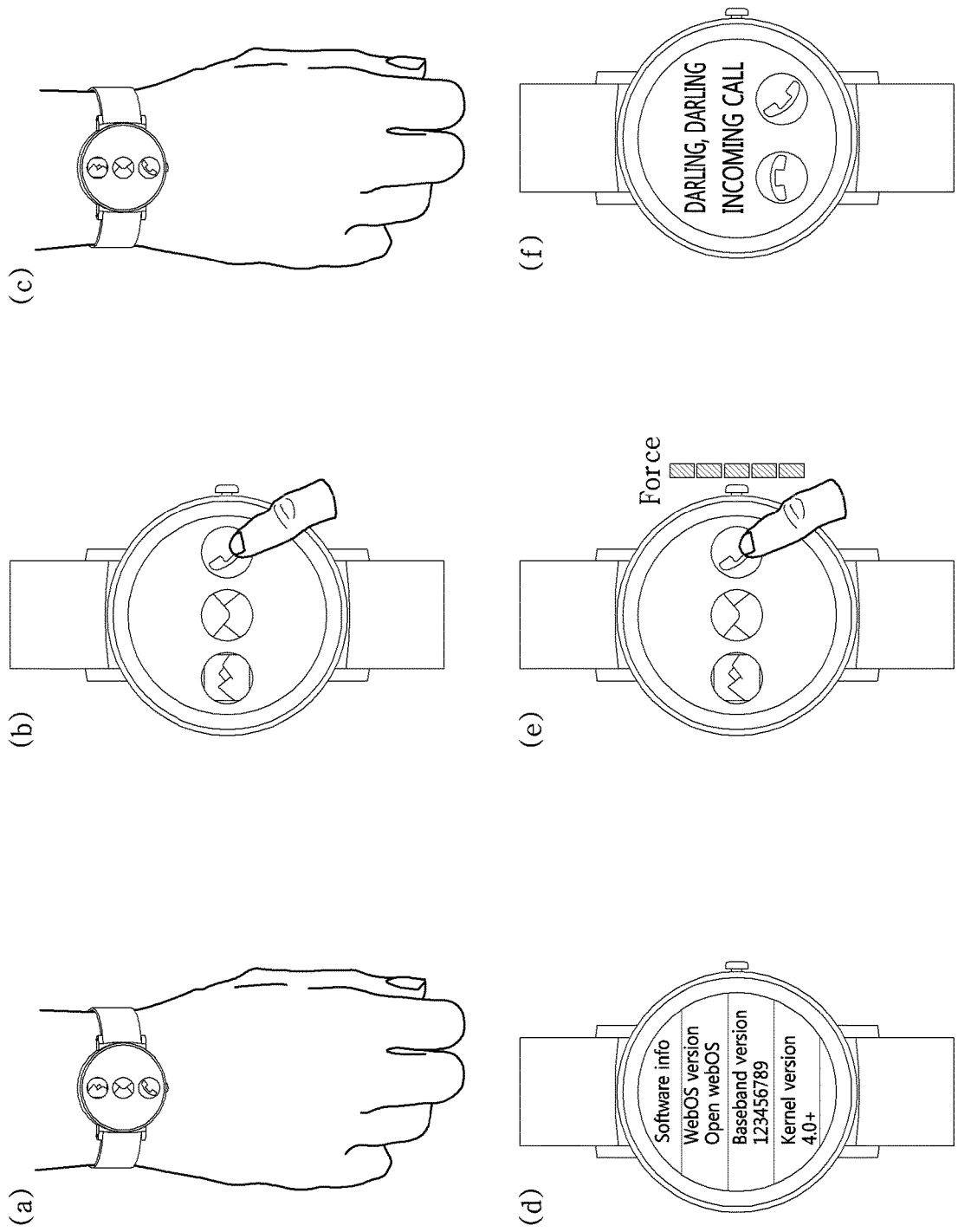
FIG. 15 illustrates exemplary screens showing that important information is not executed in a turn-on state of a screen by a touch gesture regardless of user's intentions.

FIG. 15 illustrates exemplary screens showing that important information is not executed in a turn-on state of a screen by a touch gesture regardless of user's intents.

As illustrated in FIG. 15A, a screen may be activated and thus be displayed in a state of being converted from a black screen to an ambient screen or a standby screen.

When a touch gesture regardless of user's intensions, i.e., a touch gesture having force intensity less than or equal to a critical value is input as illustrated in FIG. 15B, an icon related to information very important to a user may not be executed as illustrated in FIG. 15C.

For example, in a state in which a screen is turned on, when a user makes a gesture of shaking arms to walk along the street or waving a hand whiling chatting with a partner, the screen of the watch-type mobile type 100 often touches the clothes and the body of the user, the body of the partner, and a surrounding apparatus regardless of user's intentions.

In addition, when the touch gesture regardless of user's intensions is input as illustrated in FIG. 15B, an icon related to information not important to a user may be executed as illustrated in FIG. 15D.

The information very important to the user includes information on a phone, information on an address book, information on email, information on a document, information on a photo or a video, user personnel information, and the like.

The information not important to the user includes information on a game, information on a newspaper, information on shopping, information on a broadcast, and the like.

As described in FIG. 15C, the icon related to the information very important to the user is not executed by a touch gesture regardless of user's intentions.

In the case of the aforementioned icon, when a touch gesture having a level of force intensity greater than a critical value is applied to the screen of the watch-type mobile terminal 100, as illustrated in FIG. 15D, the information very important to the user, not just executed by the touch gesture regardless of the user's intensions, may be executed as illustrated in FIG. 15F.

Therefore, according to the present invention, although an icon is executed by a touch gesture regardless of user's intention, only when a touch gesture having a level of force intensity greater than or equal to a critical value is forcedly applied to a screen by a user, an icon related to information very important to the user may be executed, thereby preventing the exposure of information important to the user.

Figure 16:
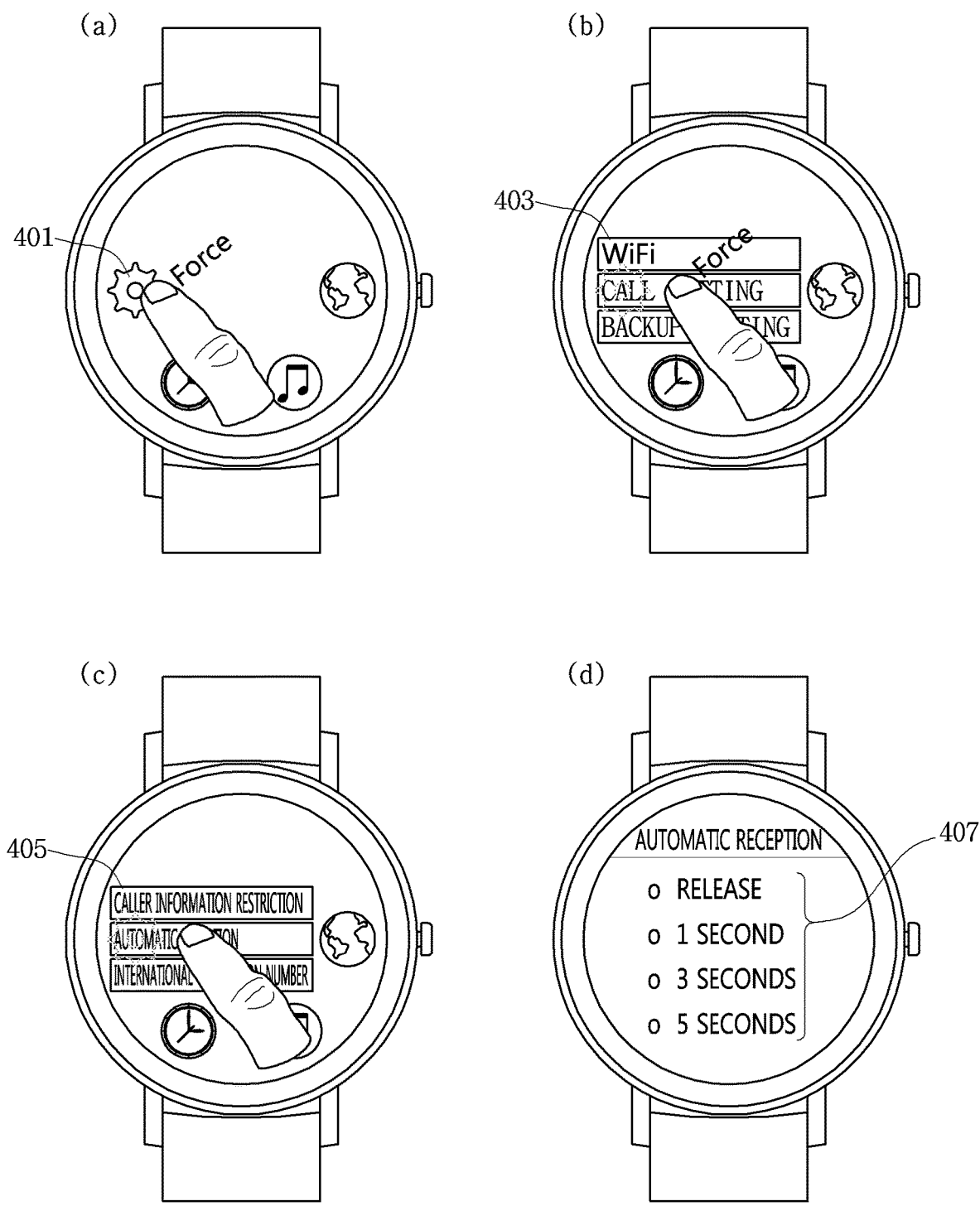
FIG. 16 illustrates exemplary screens showing that a display of a submenu of a specific icon is controlled by using touch gestures having different levels of force intensity.

FIG. 16 illustrates exemplary screens showing that a display of a submenu of a specific icon is controlled by using touch gestures having different levels of force intensity.

As illustrated in FIG. 16a, a screen may be activated, and thus, a standby screen may be displayed.

When a touch gesture having a level of force intensity greater than or equal to a critical value is input on a setting icon 401 displayed on the standby screen, as illustrated in FIG. 16B, a first sub menu 403 of a setting application may be displayed. The first sub menu 403 may include information for setting the watch-type mobile terminal 100, for example, an Wi-Fi setting object, a call setting object, a backup setting object, and the like.

The first sub menu 403 is displayed on the setting icon 401, but the present invention is not limited thereto.

In a state in which the first sub menu 403 is displayed and is touched and held, when a touch gesture having a level of force intensity greater than or equal to a critical value is applied to the call setting object of the first sub menu 403, as illustrated in FIG. 16C, a sub menu of the call setting object, i.e., a second sub menu 405 may be displayed.

The second sub menu 405 includes setting information on a call, for example, a caller information restriction object, an automatic reception object, an international connection number object, and the like.

In a state in which the second sub menu 405 is displayed and is touched and held, when a hand of a user is moved to a specific object of the second sub menu 405, for example, the automatic reception object, and then, a touch release gesture is input, as illustrated in FIG. 16D, a setting information list 407 related to the automatic reception object of the second sub menu 405 may be displayed.

For example, "release", "one second", "two seconds", and "three seconds" may be displayed as the setting information list 407 related to the automatic reception object. One selected from the "release", "one second", "two seconds", and "three seconds" may be set as setting information.

Figure 17:
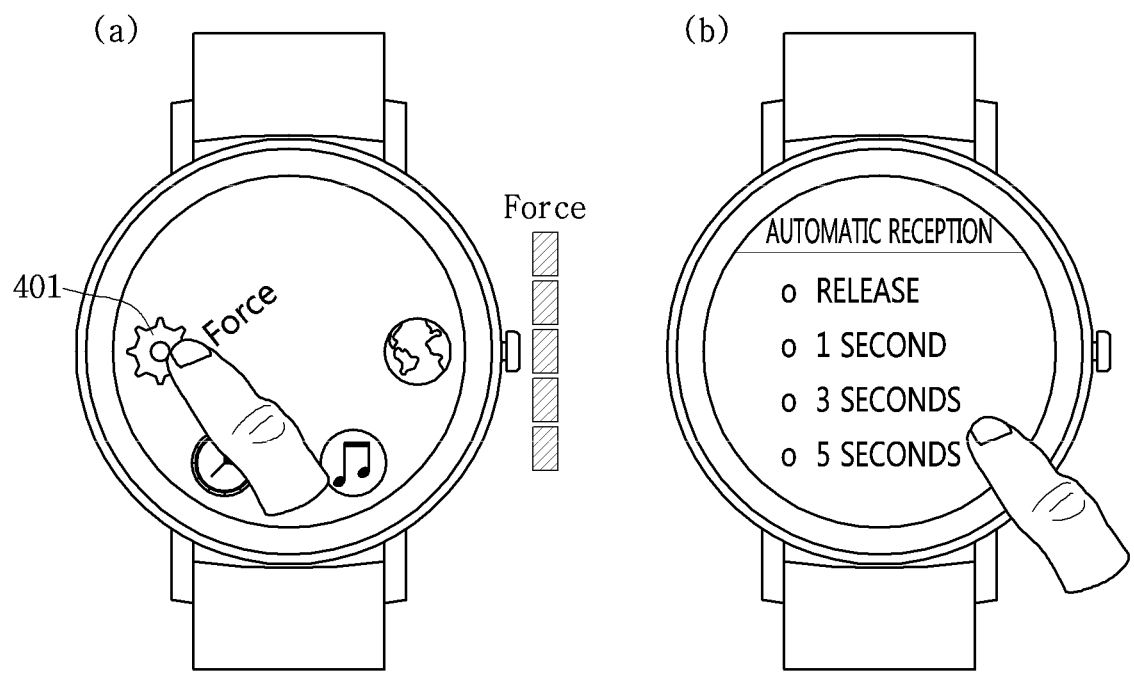
FIG. 17 illustrates exemplary screens showing that an object having a specific depth of a plurality of depths is executed by one touch gesture.

FIG. 17 illustrates exemplary screens showing that an object having a specific depth of a plurality of depths is executed by one touch gesture.

In FIG. 16, it has been possible to access a desired screen by several touch gestures.

On the contrary, in FIG. 17, it is possible to directly access a desired screen by one touch gesture.

As illustrated in FIG. 17A, in a case where a setting icon 401 is displayed on a screen, when a touch gesture is input on the setting icon 401, a screen desired by a user may be directly displayed. Here, the screen desired by the user may be a screen including the setting information list 407 related to the automatic reception object of the second sub menu 405, illustrated in FIG. 16D.

As described above, a critical value may be set such that the desired screen is displayed by one touch gesture.

Therefore, when a level of force intensity of a touch gesture on a screen by a user is greater than a critical value, a screen desired by the user may be displayed.

Although not illustrated, when a level of force intensity of a touch gesture on a screen by a user is greater than another critical value, the second sub menu 405 illustrated in FIG. 16C may be directly displayed.

According to the present invention, objects respectively having a plurality of depths may not be sequentially accessed whenever a touch gesture is input, but an object having a specific depth of the plurality of depths may be directly accessed by one touch gesture having force intensity greater than or equal to a preset critical value, thereby improving user convenience.

Figure 18:
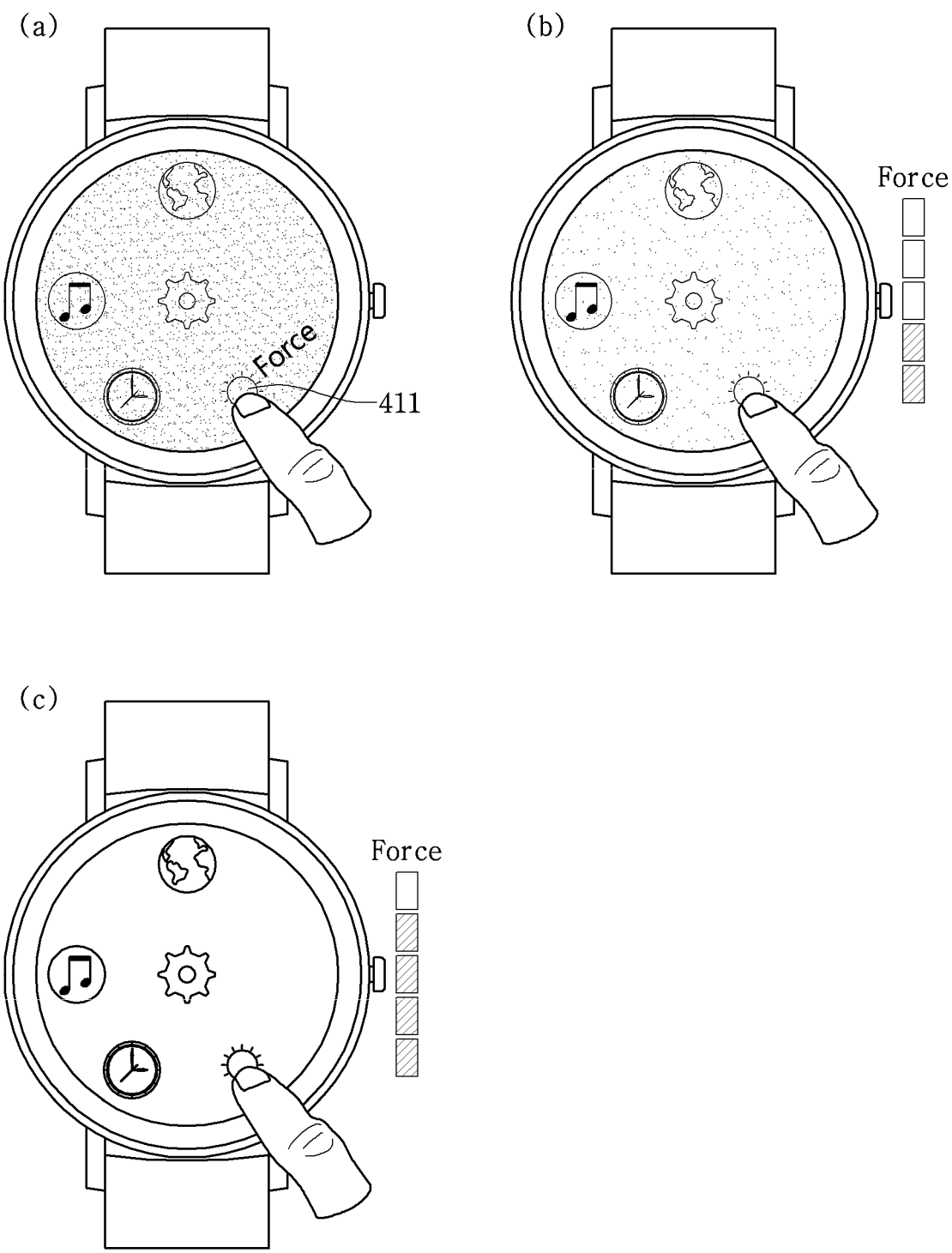
FIG. 18 illustrates exemplary screens showing that brightness is differently adjusted by using touch gestures having different levels of force intensity.

FIG. 18 illustrates exemplary screens showing that brightness is differently adjusted by using touch gestures having different levels of force intensity.

When a touch gesture having a first level of force intensity is input on a brightness icon 411 displayed on a screen, as illustrated in FIG. 18A, the screen may be adjusted to have a first gradation of brightness, as illustrated in 18B.

When a touch gesture having a second level of force intensity greater than the first level is input, as illustrated in FIG. 18C, the screen may be adjusted to have a second gradation of brightness, greater than the first gradation.

As described above, brightness of a screen may be differently adjusted by varying a level of force intensity of a touch gesture.

As force intensity of a touch gesture is increased, a screen may become brighter or darker.

Figure 19:
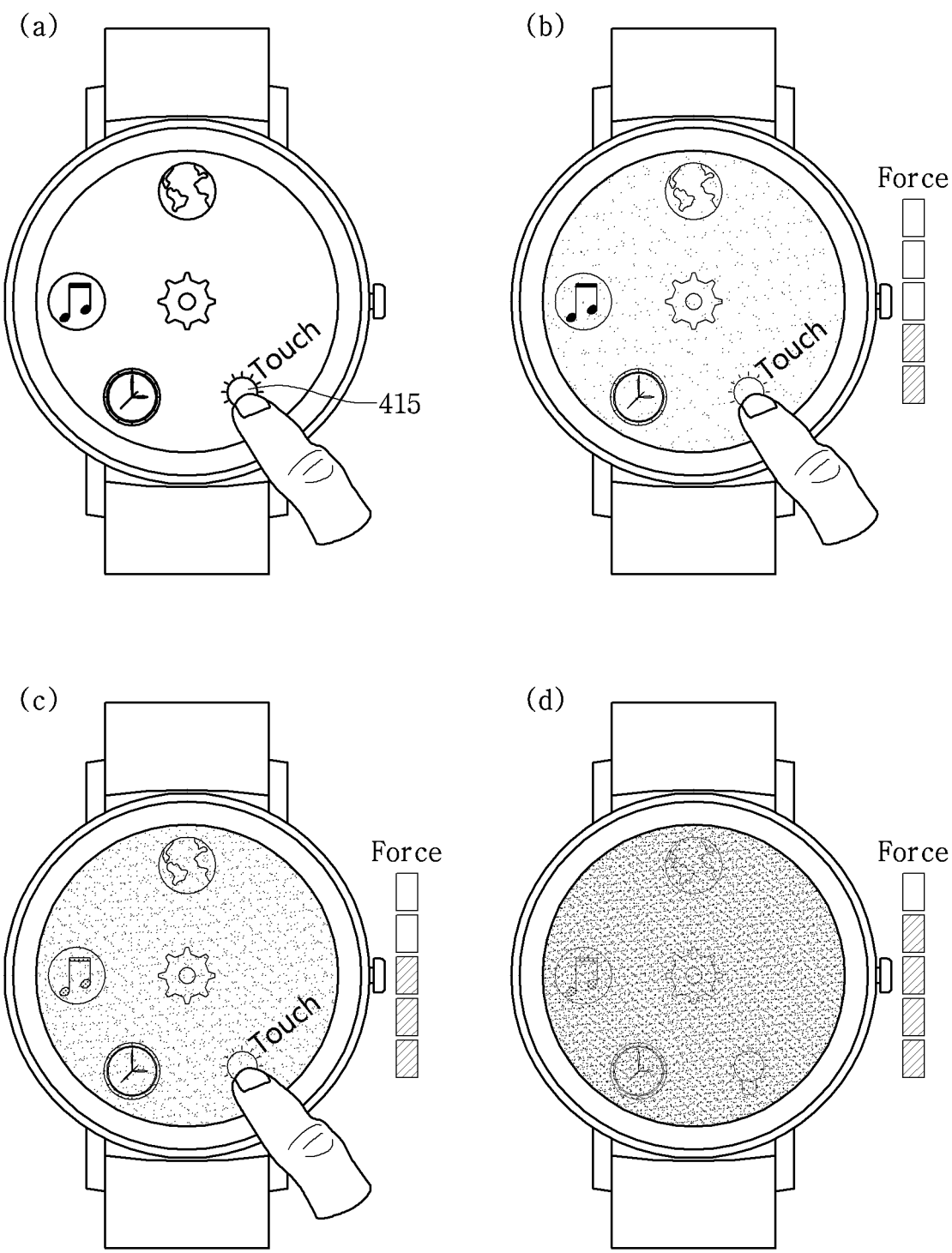
FIG. 19 illustrates exemplary screens showing that brightness is gradually decreased according to a level of force intensity of a touch gesture.

FIG. 19 illustrates exemplary screens showing that brightness is gradually decreased according to a level of force intensity of a touch gesture.

When a touch gesture having a first level of force intensity is input on a brightness icon 415 displayed on a screen having a first level of brightness, as illustrated in FIG. 19A, the screen may be adjusted to have a second level of brightness, lower than the first level, as illustrated in 19B.

Next, when a touch gesture having a second level of force intensity greater than the first level is input, as illustrated in FIG. 19C, the screen may be adjusted to have a third level of brightness, lower than the second level.

After that, when a touch gesture having a third level of force intensity greater than the second level is input, as illustrated in FIG. 19D, the screen may be adjusted to have a fourth level of brightness, lower than the third level.

As described above, as force intensity of a touch gesture, a screen may gradually become darker.

Figure 20:
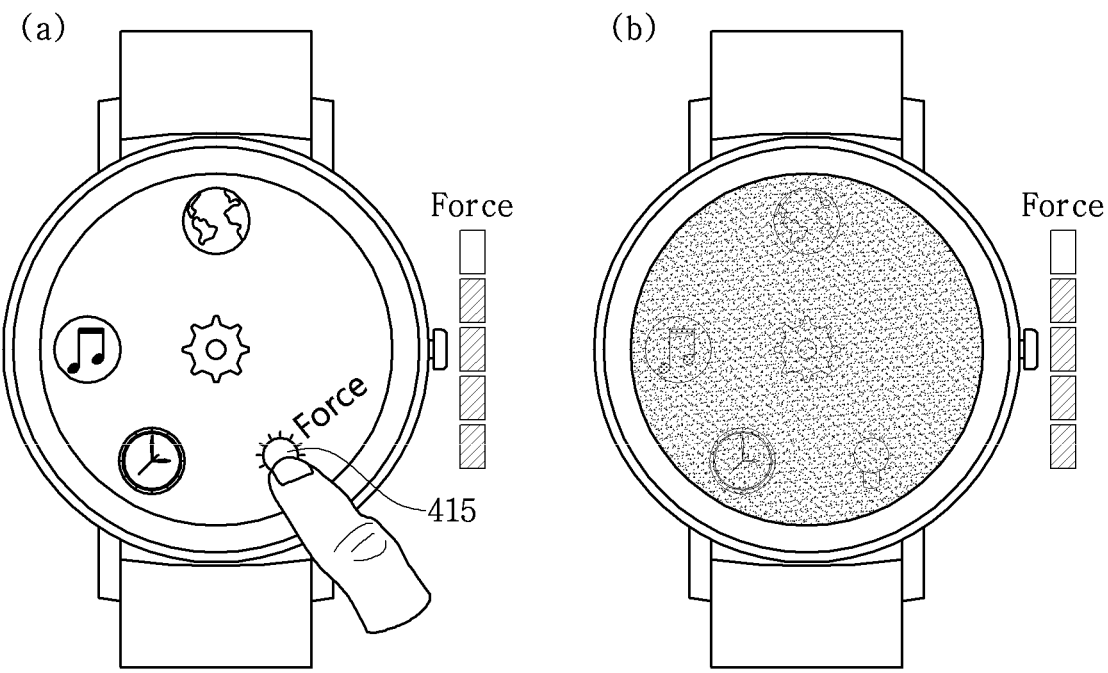
FIG. 20 illustrates exemplary screens showing that brightness is adjusted to a level desired by a user by one touch gesture.

FIG. 20 illustrates exemplary screens showing that brightness is adjusted to a level desired by a user by one touch gesture.

Instead of decreasing brightness of a screen by gradually increasing force intensity of a touch gesture as in FIG. 19, in FIG. 10, the screen may be directly darkened to a level desired by a user by one touch gesture.

That is, when a touch gesture having force intensity greater than or equal to a preset critical value is input on a brightness icon 415 displayed on a screen having a first level of brightness, as illustrated in FIG. 120A, the screen may be directly darkened to brightness desired by a user, for example, brightness illustrated in FIG. 19D.

According to the present invention, brightness of a screen is not only adjusted according to a level of force intensity of a touch gesture. That is, according to the present invention, a level of a sound or a vibration may be differently adjusted according to a level of force intensity of a touch gesture.

According to the present invention, various operations or functions may be executed according to a level of force intensity of a touch gesture.

Figure 21:
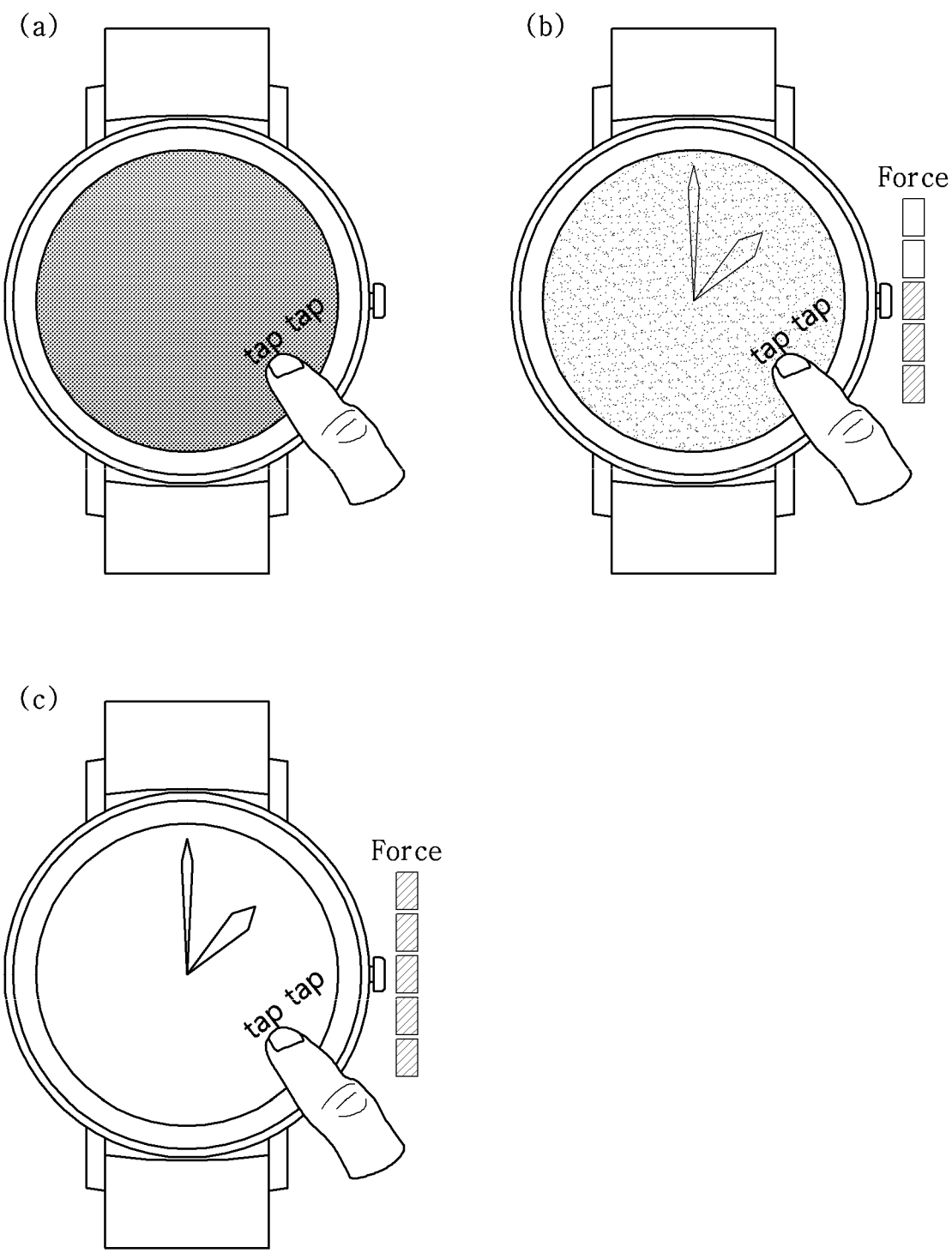
FIG. 21 illustrates exemplary screens showing that brightness of a screen is adjusted according to a level of force intensity of a double tap (knock-on) gesture when the double tap gesture is input so as to turn on the screen in a state of being turned off.

FIG. 21 illustrates exemplary screens showing that brightness of a screen is adjusted according to a level of force intensity of a double tap (knock-on) gesture when the double tap gesture is input so as to turn on the screen in a state of being turned off.

As illustrated in FIG. 21A, when a screen is turned off, i.e., power is not supplied to the screen, the screen may become a black screen.

When a double tap gesture is input on the black screen, the screen may be turned on and thus be displayed in a state of being converted from the black screen to an ambient screen or a standby screen.

As illustrated in FIG. 21B, when a double tap gesture having a first level of force intensity is input on the black screen, the screen may be adjusted to have a first level of brightness.

As illustrated in FIG. 21C, when a double tap gesture having a second level of force intensity is input on the black screen, the screen may be adjusted to have a second level of brightness.

The second level of force intensity may be greater than the first level of force intensity.

The second level of brightness may be brighter than the first level of brightness.

For example, the first level of brightness may be about 60% of maximum brightness and the second level of brightness may be the maximum brightness, but the present invention is not limited thereto.

In FIGS. 21A to 21C, it has been described to be limited to a case where brightness of the screen has two levels, i.e., the first level of brightness and the second level of brightness. However, the brightness of the screen may be subdivides into levels more than the two levels and be adjusted.

Figure 22:
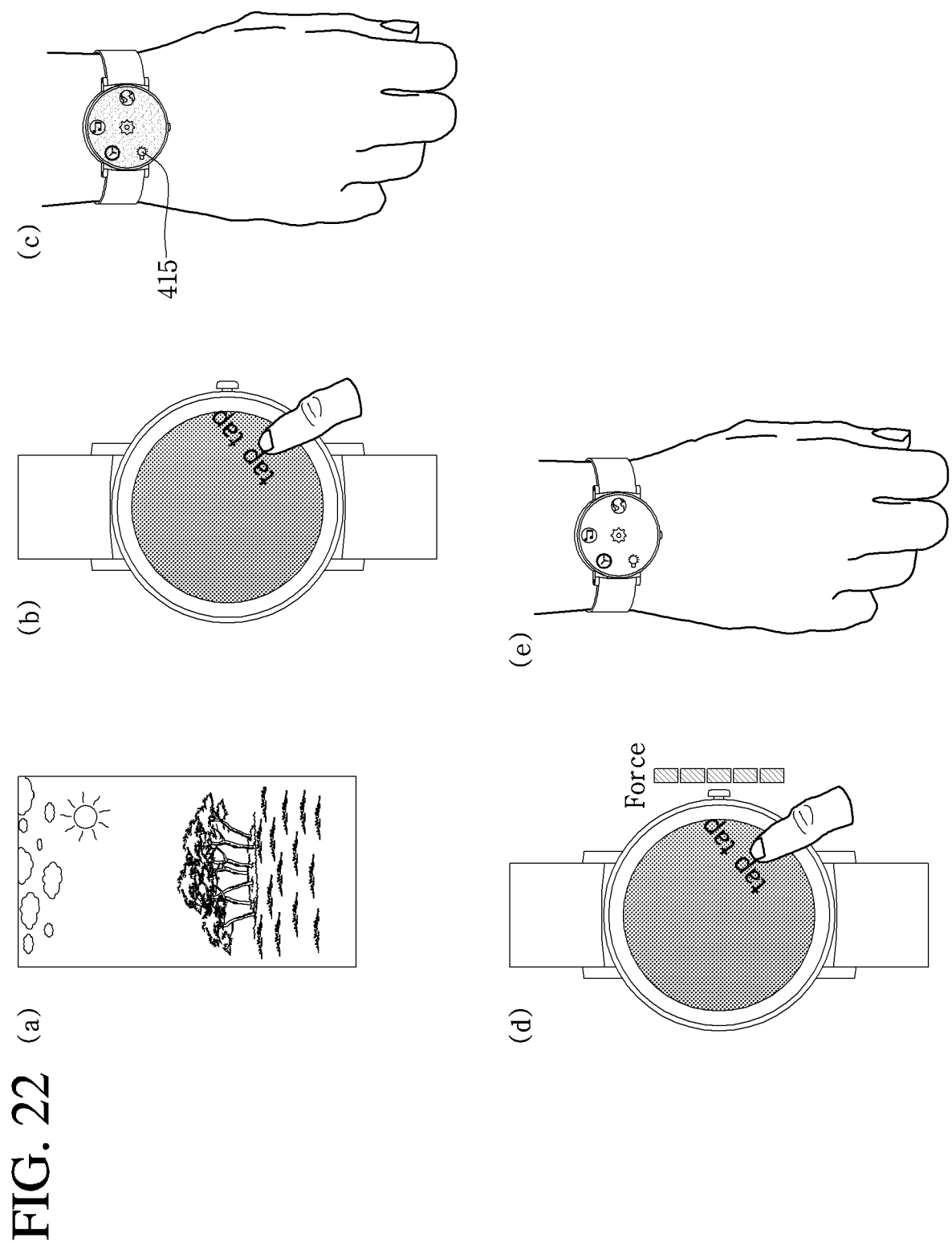
FIG. 22 illustrates exemplary screens showing a method of allowing a screen to appear brighter in the daytime open air.

FIG. 22 illustrates exemplary screens showing a method of allowing a screen to appear brighter in the daytime open air.

When a double tap gesture is input as illustrated in FIG. 21B in the daytime open air as illustrated in FIG. 21A, a screen may be turned on as illustrated in FIG. 21C.

In this case, since ambient brightness, i.e., brightness of the sun is brighter than brightness of the screen, it may be difficult to identify information provided on the screen.

In order to further brighten the screen, since it is necessary to additionally input a touch gesture on a brightness icon 415 as illustrated in FIG. 18, an additional gesture of a user may be required to cause inconvenience to the user.

In order to solve the inconvenience, when a double tap gesture having force intensity greater than or equal to a critical value is input as illustrated in FIG. 22D, a screen may be adjusted to have brightness brighter than ambient brightness while being turned on, as illustrated in FIG. 22E.

As described above, according to the present invention, since a screen is directly adjustable to have brightness brighter than that of a bright space by inputting one double tap gesture, an additional gesture for adjusting the screen to have brightness desired by a user after turning the screen may not be required to improve user convenience.

Figure 23:
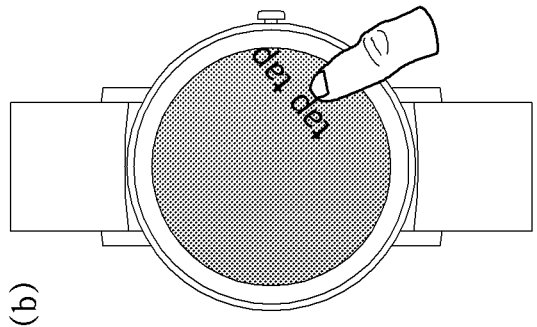
FIG. 23 illustrates exemplary screens showing a method of allowing a screen to appear darker in the night time or in dark environments.
Figure 23:
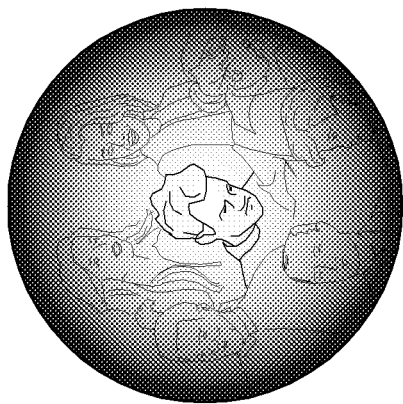
Figure 23:
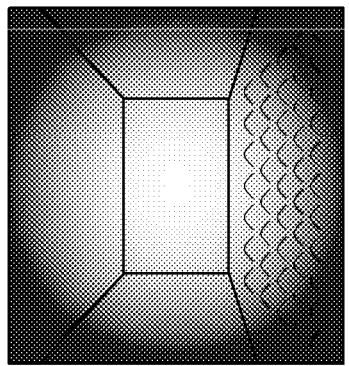
Figure 23:
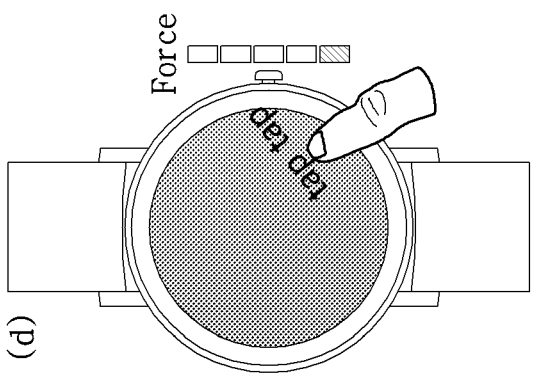
Figure 23:
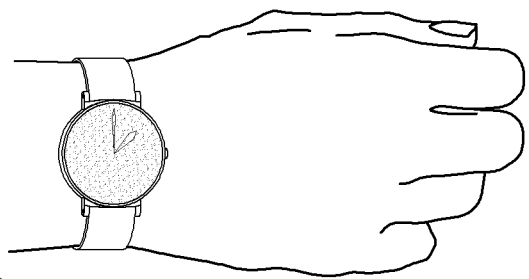

FIG. 23 illustrates exemplary screens showing a method of allowing a screen to appear darker in the night time or in dark environments.

As illustrated in FIG. 23A, when a user views a film in a dark space, for example, i.e., a theater, the theater is considerably dark.

In this case, the screen of the watch-type mobile terminal 100 worn on a wrist on the user may be in a black state.

As illustrated in FIG. 23B, when a double tap gesture is input on the screen to view the screen of the watch-type mobile terminal 100, the screen of the watch-type mobile terminal 100 may be turned on, and thus, a black screen may be converted into an ambient screen or a standby screen.

In this case, as illustrated in FIG. 23C, when the screen of the watch-type mobile terminal 100 is turned on in the theater, due to brightness of the screen, the people around the user are hindered in viewing a film.

In order to solve such a problem, when a double tap gesture having force intensity greater than or equal to a critical value is input as illustrated in FIG. 23D, the screen may be adjusted to have a level of brightness, lower than a preset level of brightness, as illustrated in FIG. 23E. Since the screen has a low level of brightness as described above, the people around the user may not recognize the screen of the watch-type mobile terminal 100 and thus may not be hindered.

As described above, since a screen may be directly adjusted to have brightness darker than that of a dark space by inputting one double tap gesture, an additional gesture for adjusting the screen to have brightness desired by a user after turning the screen may not be required to improve user convenience Here, the critical value described in FIG. 22 may be different from the critical value described in FIG. 23.

The critical value described in FIG. 22 is referred to as a first critical value, and the critical value described in FIG. 23 is referred to as a second critical value.

When a screen is adjusted to a dark screen as a level of force intensity of a double tap gesture is lowered, the first critical value may be greater than the second critical value.

For example, when a double tap gesture having force intensity greater than or equal to the second critical value is input as illustrated in FIG. 23D, a screen may be adjusted to have brightness higher than a black gradation by about 10 gradations to about 50 gradations.

For example, when a double tap gesture having force intensity greater than or equal to the first critical value is input as illustrated in FIG. 22D, a screen may be adjusted to have relatively high brightness, i.e., brightness brighter than brightness of the sun.

Figure 24:
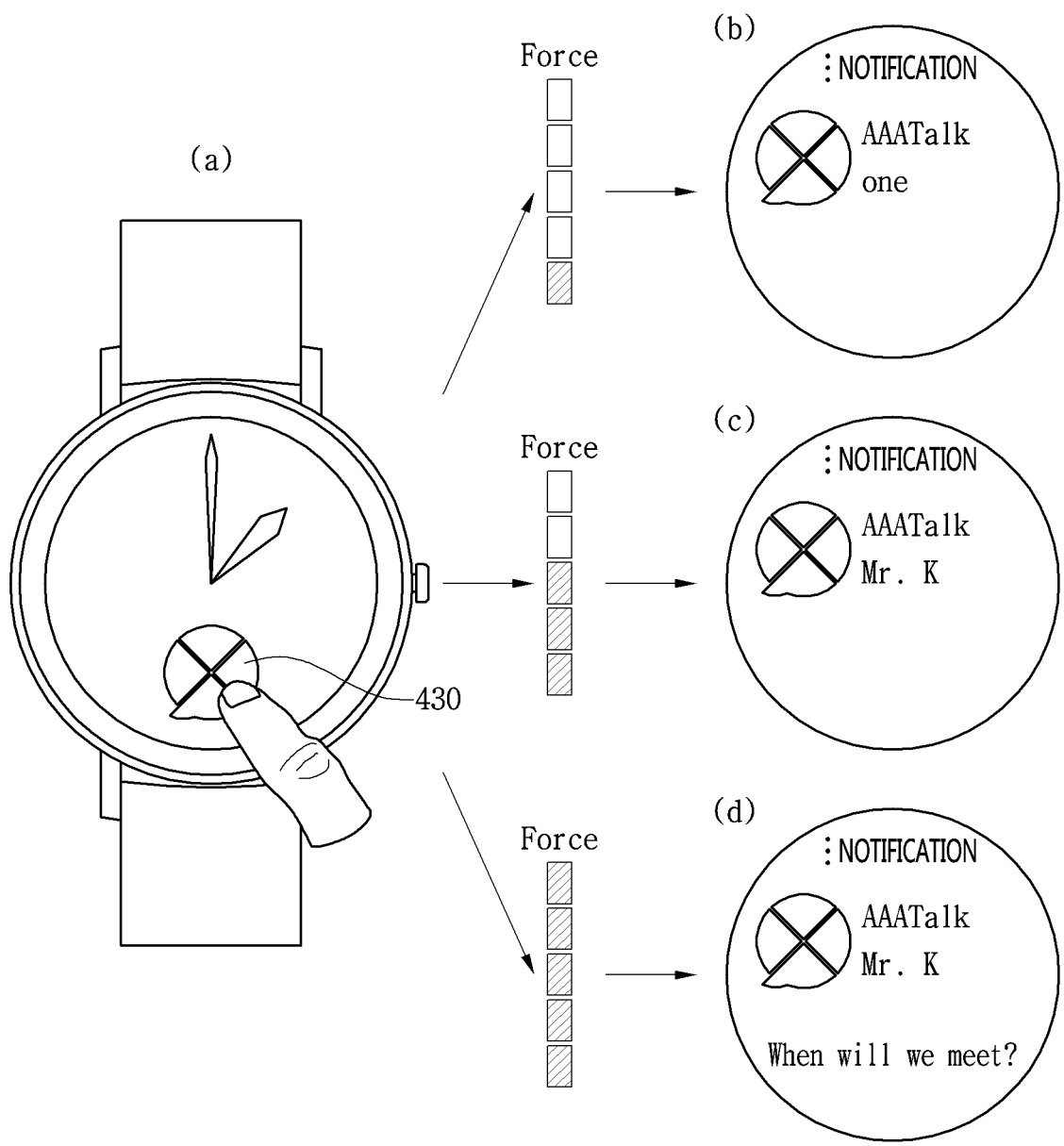
FIG. 24 illustrates exemplary screens showing that a degree of information is differently displayed according to a level of force intensity of a touch gesture.

FIG. 24 illustrates exemplary screens showing that a degree of information is differently displayed according to a level of force intensity of a touch gesture.

As illustrated in FIG. 24A, an information icon 430 may be displayed on a screen.

The screen may be an ambient screen or a standby screen.

For example, the information icon 430 may be an SNS messenger icon, a mail icon, a telephone icon, and the like.

For example, when force intensity of a touch gesture applied to the information icon 430 displayed on the screen has a first level, as illustrated in FIG. 24B, the number of information receptions may only be displayed.

A user may confirm the number of information receptions related to the information icon 430 through the touch gesture having the first level of force intensity.

For example, when force intensity of a touch gesture applied to the information icon 430 displayed on the screen has a second level greater than a first level, as illustrated in FIG. 24C, information on a called party may be displayed.

Since the user is capable of confirming who the information on the called party related to the information icon 430 is, through the touch gesture having the second level of force intensity, the user may determine whether the called party is a called party important to the user and thus may take follow-up action.

When three pieces of information are received, each of three contact information objects may be displayed in a list form by the touch gesture having the second level of force intensity. In a case where there is contact information of three pieces of contact information, additional information of which is to be viewed, when a touch gesture with respect to a corresponding contact information object is added, as illustrated in FIG. 24D, information transmitted by a corresponding called party may be displayed.

Therefore, the user may confirm a called party who transmits information, through the touch gesture having the second level of force intensity, and may confirm information transmitted by a corresponding called party, through an additional touch gesture with respect to a specific called party.

For example, when force intensity of a touch gesture applied to the information icon 430 displayed on the screen has a third level greater than the second level, as illustrated in FIG. 24D, contact information as well as information transmitted by the corresponding called party may be displayed.

Therefore, according to the present invention, a degree of information may be differently displayed according to force intensity of a touch gesture, thereby expanding the degrees of freedom for information selection of a user.

The present invention mentioned in the foregoing description may be implemented using a machine-readable medium having instructions stored thereon for execution by a processor to perform various methods presented herein. Examples of possible machine-readable mediums include HDD (Hard Disk Drive), SSD (Solid State Disk), SDD (Silicon Disk Drive), ROM, RAM, CD-ROM, a magnetic tape, a floppy disk, an optical data storage device, the other types of storage mediums presented herein, and combinations thereof. If desired, the machine-readable medium may be realized in the form of a carrier wave (for example, a transmission over the Internet). The processor may include the controller 180 of the mobile terminal. The foregoing embodiments are merely exemplary and are not to be considered as limiting the present disclosure. This description is intended to be illustrative, and not to limit the scope of the claims. Many alternatives, modifications, and variations will be apparent to those skilled in the art. The features, structures, methods, and other characteristics of the exemplary embodiments described herein may be combined in various ways to obtain additional and/or alternative exemplary embodiments. As the present features may be embodied in several forms without departing from the characteristics thereof, it should also be understood that the above-described embodiments are not limited by any of the details of the foregoing description, unless otherwise specified, but rather should be considered broadly within its scope as defined in the appended claims, and therefore all changes and modifications that fall within the metes and bounds of the claims, or equivalents of such metes and bounds, are therefore intended to be embraced by the appended claims.

INDUSTRIAL APPLICABILITY

The present invention may be applied to wearable devices including a watch-type mobile terminal.

The invention claimed is:

1. A watch-type mobile terminal comprising:
    a touch screen configured to sense a touch gesture and output information;
    a force sensor configured to sense intensity of the touch gesture applied to the touch screen;
    an acceleration sensor; and
    a controller configured to:
        determine a direction and an acceleration of the mobile terminal based on values obtained from the acceleration sensor;
        determine whether the touch screen is facing a user's eyes based on the determined direction of the mobile terminal; and
        execute at least one operation based on an activation status of the touch screen, the sensed intensity of the touch gesture, and whether the touch screen is facing the user's eyes,
    wherein executing the at least one operation comprises:
        activating the touch screen when a level of the sensed intensity of the touch gesture is greater than or equal to a predetermined activation threshold value while the touch screen is in an inactive state; and
        changing at least one of a brightness level of the touch screen, a sound level, or a vibration level in response to change of the sensed intensity of the touch gesture while the touch screen is in an active state such that the at least one of the brightness level of the touch screen, the sound level, or the vibration level is changed each time when the sensed intensity of the touch gesture is changed from one level to another level.

2. The watch-type mobile terminal according to claim 1, wherein the controller is further configured to convert the touch screen from a black screen to an ambient screen or a standby screen when the touch screen faces the user's eyes.

3. The watch-type mobile terminal according to claim 1, wherein the controller is further configured to maintain a black screen of the touch screen when the touch screen does not face the user's eyes.

4. The watch-type mobile terminal according to claim 3, wherein the controller is further configured to convert the black screen to an ambient screen or a standby screen when the sensed intensity of the touch gesture is greater than a predetermined value.

5. The watch-type mobile terminal according to claim 1, wherein the controller is further configured to set the predetermined activation threshold value as a first value when the touch screen faces the user's eyes.

6. The watch-type mobile terminal according to claim 5, wherein the controller is further configured to set the predetermined activation threshold value as a second value when the touch screen does not face the user's eyes.

7. The watch-type mobile terminal according to claim 6, wherein each of the first value and the second value is a reference capacitance value for recognizing the touch gesture.

8. The watch-type mobile terminal according to claim 6, wherein the second value is greater than the first value.

9. The watch-type mobile terminal according to claim 1, wherein the controller is further configured to execute a preset operation when the sensed intensity of the touch gesture is greater than a predetermined value while the touch screen is in the active state.

10. The watch-type mobile terminal according to claim 1, wherein the at least one operation comprises sequentially displaying sub-menus of a specific icon, each of the sub-menus having a depth among a plurality of depths.

11. The watch-type mobile terminal according to claim 1, wherein the controller is further configured to:
convert the touch screen from a black screen to an ambient screen or a standby screen; and
increase or decrease a level of brightness, sound or vibration when sensed intensity of a double tap gesture applied to the touch screen is changed.

12. The watch-type mobile terminal according to claim 1, wherein the controller is further configured to:
convert the touch screen from a black screen to an ambient screen or a standby screen; and
adjust brightness of the touch screen such that the adjusted brightness is brighter than a preset brightness when sensed intensity of a double tap gesture applied to the touch screen is greater than a predetermined value.

13. The watch-type mobile terminal according to claim 1, wherein the controller is further configured to display different information on the touch screen according to a change in the sensed intensity of the touch gesture while the touch screen is in the active state.

14. The watch-type mobile terminal according to claim 1, wherein the controller is further configured to execute different functions according to a sensed acceleration of a gesture that causes the mobile terminal to face the user's eyes.

15. The watch-type mobile terminal according to claim 14, wherein the controller is further configured to convert the touch screen from a black screen to an ambient screen or a standby screen when the sensed acceleration of the gesture is greater than a predetermined value.

16. The watch-type mobile terminal according to claim 14, wherein the controller is further configured to maintain a black screen of the touch screen when the sensed acceleration of the gesture is smaller than a predetermined value.

17. The watch-type mobile terminal according to claim 16, wherein the controller is further configured to convert the black screen to an ambient screen or a standby screen when the sensed acceleration of the gesture is greater than the predetermined value.

18. A method of controlling watch-type mobile terminal, the method comprising:
sensing intensity of a force applied to a touch screen of the mobile terminal;
sensing a direction and acceleration of the mobile terminal;
activating the touch screen according a direction faced by the mobile terminal;
adjusting touch sensitivity of the touch screen based on whether the touch screen faces a user's eyes; and
maintaining a black screen of the touch screen or converting the black screen to an ambient screen or a standby screen based on whether the touch screen faces the user's eyes.

19. A method of controlling watch-type mobile terminal, the method comprising:
sensing intensity of a touch gesture applied to a touch screen of the mobile terminal;
determining a direction and an acceleration of the mobile terminal based on values obtained from an acceleration sensor of the mobile terminal;
determining whether the touch screen is facing a user's eyes based on the determined direction of the mobile terminal; and
executing at least one operation based on an activation status of the touch screen, the sensed intensity of the touch gesture, and whether the touch screen is facing the user's eyes,
wherein executing the at least one operation comprises:
activating the touch screen when the sensed intensity of the touch gesture is greater than or equal to a predetermined activation threshold value while the touch screen is in an inactive state; and
changing at least one of a brightness level of the touch screen, a sound level, or a vibration level in response to change of the sensed intensity of the touch gesture while the touch screen is in an active state such that the at least one of the brightness level of the touch screen, the sound level, or the vibration level is changed each time when the sensed intensity of the touch gesture is changed from one level to another level.

* * * * *